US012778499B2

(12) United States Patent
Troxell et al.

(10) Patent No.: US 12,778,499 B2
(45) Date of Patent: Nov. 3, 2026

(54) IMPLANTABLE RF SENSOR FOR BIOFILM DETECTION

(71) Applicant: GLOBUS MEDICAL, INC., Audubon, PA (US)

(72) Inventors: Paden Troxell, Conshohocken, PA (US); David C. Paul, Phoenixville, PA (US)

(73) Assignee: Globus Medical Inc., Audubon, PA (US)

( * ) Notice: Subject to any disclaimer, the term of this patent is extended or adjusted under 35 U.S.C. 154(b) by 394 days.

(21) Appl. No.: 18/478,012

(22) Filed: Sep. 29, 2023

(65) Prior Publication Data

US 2025/0107752 A1 Apr. 3, 2025

Related U.S. Application Data

(63) Continuation of application No. 18/477,841, filed on Sep. 29, 2023.

(51) Int. Cl.
*A61B 5/00* (2006.01)

(52) U.S. Cl.
CPC .......... *A61B 5/4851* (2013.01); *A61B 5/0031* (2013.01); *A61B 5/686* (2013.01)

(58) Field of Classification Search
CPC ..... A61B 5/4851; A61B 5/0031; A61B 5/686; A61B 5/0507
See application file for complete search history.

(56) References Cited

U.S. PATENT DOCUMENTS

| | | | |
|---|---|---|---|
| 4,150,293 | A | 4/1979 | Franke |
| 5,246,010 | A | 9/1993 | Gazzara et al. |
| 5,354,314 | A | 10/1994 | Hardy et al. |
| 5,397,323 | A | 3/1995 | Taylor et al. |
| 5,598,453 | A | 1/1997 | Baba et al. |
| 5,772,594 | A | 6/1998 | Barrick |
| 5,791,908 | A | 8/1998 | Gillio |
| 5,820,559 | A | 10/1998 | Ng et al. |
| 5,825,982 | A | 10/1998 | Wright et al. |
| 5,887,121 | A | 3/1999 | Funda et al. |
| 5,911,449 | A | 6/1999 | Daniele et al. |
| 5,951,475 | A | 9/1999 | Gueziec et al. |
| 5,987,960 | A | 11/1999 | Messner et al. |
| 6,012,216 | A | 1/2000 | Esteves et al. |
| 6,031,888 | A | 2/2000 | Ivan et al. |
| 6,033,415 | A | 3/2000 | Mittelstadt et al. |
| 6,080,181 | A | 6/2000 | Jensen et al. |

(Continued)

OTHER PUBLICATIONS

US 8,231,638 B2, 07/2012, Swarup et al. (withdrawn)

(Continued)

*Primary Examiner* — Joseph M Dietrich

(57) ABSTRACT

A medical implant includes an implant component configured to be implanted in a patient, a radio frequency (RF) transmit antenna in the implant component and configured to transmit a RF signal, and circuitry within the implant component. The circuitry is operative to generate the RF signal to the RF transmit antenna, determine a characteristic of attenuation of the RF signal when the RF transmit antenna is transmitting the RF signal while implanted in the patient, and detect presence of biofilm on the medical implant based on the characteristic of attenuation of the RF signal.

17 Claims, 10 Drawing Sheets

(56) References Cited

U.S. PATENT DOCUMENTS

| | | | |
|---|---|---|---|
| 6,106,511 | A | 8/2000 | Jensen |
| 6,122,541 | A | 9/2000 | Cosman et al. |
| 6,144,875 | A | 11/2000 | Schweikard et al. |
| 6,157,853 | A | 12/2000 | Blume et al. |
| 6,167,145 | A | 12/2000 | Foley et al. |
| 6,167,292 | A | 12/2000 | Badano et al. |
| 6,201,984 | B1 | 3/2001 | Funda et al. |
| 6,203,196 | B1 | 3/2001 | Meyer et al. |
| 6,205,411 | B1 | 3/2001 | DiGioia, III et al. |
| 6,212,419 | B1 | 4/2001 | Blume et al. |
| 6,231,565 | B1 | 5/2001 | Tovey et al. |
| 6,236,875 | B1 | 5/2001 | Bucholz et al. |
| 6,246,900 | B1 | 6/2001 | Cosman et al. |
| 6,301,495 | B1 | 10/2001 | Gueziec et al. |
| 6,306,126 | B1 | 10/2001 | Montezuma |
| 6,312,435 | B1 | 11/2001 | Wallace et al. |
| 6,314,311 | B1 | 11/2001 | Williams et al. |
| 6,320,929 | B1 | 11/2001 | Von Der Haar |
| 6,322,567 | B1 | 11/2001 | Mittelstadt et al. |
| 6,325,808 | B1 | 12/2001 | Bernard et al. |
| 6,340,363 | B1 | 1/2002 | Bolger et al. |
| 6,377,011 | B1 | 4/2002 | Ben-Ur |
| 6,379,302 | B1 | 4/2002 | Kessman et al. |
| 6,402,762 | B2 | 6/2002 | Hunter et al. |
| 6,424,885 | B1 | 7/2002 | Niemeyer et al. |
| 6,447,503 | B1 | 9/2002 | Wynne et al. |
| 6,451,027 | B1 | 9/2002 | Cooper et al. |
| 6,477,400 | B1 | 11/2002 | Barrick |
| 6,484,049 | B1 | 11/2002 | Seeley et al. |
| 6,487,267 | B1 | 11/2002 | Wolter |
| 6,490,467 | B1 | 12/2002 | Bucholz et al. |
| 6,490,475 | B1 | 12/2002 | Seeley et al. |
| 6,499,488 | B1 | 12/2002 | Hunter et al. |
| 6,501,981 | B1 | 12/2002 | Schweikard et al. |
| 6,507,751 | B2 | 1/2003 | Blume et al. |
| 6,535,756 | B1 | 3/2003 | Simon et al. |
| 6,560,354 | B1 | 5/2003 | Maurer, Jr. et al. |
| 6,565,554 | B1 | 5/2003 | Niemeyer |
| 6,587,750 | B2 | 7/2003 | Gerbi et al. |
| 6,614,453 | B1 | 9/2003 | Suri et al. |
| 6,614,871 | B1 | 9/2003 | Kobiki et al. |
| 6,619,840 | B2 | 9/2003 | Rasche et al. |
| 6,636,757 | B1 | 10/2003 | Jascob et al. |
| 6,645,196 | B1 | 11/2003 | Nixon et al. |
| 6,666,579 | B2 | 12/2003 | Jensen |
| 6,669,635 | B2 | 12/2003 | Kessman et al. |
| 6,701,173 | B2 | 3/2004 | Nowinski et al. |
| 6,757,068 | B2 | 6/2004 | Foxlin |
| 6,782,287 | B2 | 8/2004 | Grzeszczuk et al. |
| 6,783,524 | B2 | 8/2004 | Anderson et al. |
| 6,786,896 | B1 | 9/2004 | Madhani et al. |
| 6,788,018 | B1 | 9/2004 | Blumenkranz |
| 6,804,581 | B2 | 10/2004 | Wang et al. |
| 6,823,207 | B1 | 11/2004 | Jensen et al. |
| 6,827,351 | B2 | 12/2004 | Graziani et al. |
| 6,837,892 | B2 | 1/2005 | Shoham |
| 6,839,612 | B2 | 1/2005 | Sanchez et al. |
| 6,856,826 | B2 | 2/2005 | Seeley et al. |
| 6,856,827 | B2 | 2/2005 | Seeley et al. |
| 6,879,880 | B2 | 4/2005 | Nowlin et al. |
| 6,892,090 | B2 | 5/2005 | Verard et al. |
| 6,920,347 | B2 | 7/2005 | Simon et al. |
| 6,922,632 | B2 | 7/2005 | Foxlin |
| 6,968,224 | B2 | 11/2005 | Kessman et al. |
| 6,978,166 | B2 | 12/2005 | Foley et al. |
| 6,988,009 | B2 | 1/2006 | Grimm et al. |
| 6,991,627 | B2 | 1/2006 | Madhani et al. |
| 6,996,487 | B2 | 2/2006 | Jutras et al. |
| 6,999,852 | B2 | 2/2006 | Green |
| 7,007,699 | B2 | 3/2006 | Martinelli et al. |
| 7,016,457 | B1 | 3/2006 | Senzig et al. |
| 7,043,961 | B2 | 5/2006 | Pandey et al. |
| 7,062,006 | B1 | 6/2006 | Pelc et al. |
| 7,063,705 | B2 | 6/2006 | Young et al. |
| 7,072,707 | B2 | 7/2006 | Galloway, Jr. et al. |
| 7,083,615 | B2 | 8/2006 | Peterson et al. |
| 7,097,640 | B2 | 8/2006 | Wang et al. |
| 7,099,428 | B2 | 8/2006 | Clinthorne et al. |
| 7,108,421 | B2 | 9/2006 | Gregerson et al. |
| 7,130,676 | B2 | 10/2006 | Barrick |
| 7,139,418 | B2 | 11/2006 | Abovitz et al. |
| 7,139,601 | B2 | 11/2006 | Bucholz et al. |
| 7,155,316 | B2 | 12/2006 | Sutherland et al. |
| 7,164,968 | B2 | 1/2007 | Treat et al. |
| 7,167,738 | B2 | 1/2007 | Schweikard et al. |
| 7,169,141 | B2 | 1/2007 | Brock et al. |
| 7,172,627 | B2 | 2/2007 | Fiere et al. |
| 7,194,120 | B2 | 3/2007 | Wicker et al. |
| 7,197,107 | B2 | 3/2007 | Arai et al. |
| 7,231,014 | B2 | 6/2007 | Levy |
| 7,231,063 | B2 | 6/2007 | Naimark et al. |
| 7,239,940 | B2 | 7/2007 | Wang et al. |
| 7,248,914 | B2 | 7/2007 | Hastings et al. |
| 7,301,648 | B2 | 11/2007 | Foxlin |
| 7,302,288 | B1 | 11/2007 | Schellenberg |
| 7,313,430 | B2 | 12/2007 | Urquhart et al. |
| 7,318,805 | B2 | 1/2008 | Schweikard et al. |
| 7,318,827 | B2 | 1/2008 | Leitner et al. |
| 7,319,897 | B2 | 1/2008 | Leitner et al. |
| 7,324,623 | B2 | 1/2008 | Heuscher et al. |
| 7,327,865 | B2 | 2/2008 | Fu et al. |
| 7,331,967 | B2 | 2/2008 | Lee et al. |
| 7,333,642 | B2 | 2/2008 | Green |
| 7,339,341 | B2 | 3/2008 | Oleynikov et al. |
| 7,366,562 | B2 | 4/2008 | Dukesherer et al. |
| 7,379,790 | B2 | 5/2008 | Toth et al. |
| 7,386,365 | B2 | 6/2008 | Nixon |
| 7,422,592 | B2 | 9/2008 | Morley et al. |
| 7,435,216 | B2 | 10/2008 | Kwon et al. |
| 7,440,793 | B2 | 10/2008 | Chauhan et al. |
| 7,460,637 | B2 | 12/2008 | Clinthorne et al. |
| 7,466,303 | B2 | 12/2008 | Yi et al. |
| 7,493,153 | B2 | 2/2009 | Ahmed et al. |
| 7,505,617 | B2 | 3/2009 | Fu et al. |
| 7,533,892 | B2 | 5/2009 | Schena et al. |
| 7,542,791 | B2 | 6/2009 | Mire et al. |
| 7,555,331 | B2 | 6/2009 | Viswanathan |
| 7,567,834 | B2 | 7/2009 | Clayton et al. |
| 7,594,912 | B2 | 9/2009 | Cooper et al. |
| 7,606,613 | B2 | 10/2009 | Simon et al. |
| 7,607,440 | B2 | 10/2009 | Coste-Maniere et al. |
| 7,623,902 | B2 | 11/2009 | Pacheco |
| 7,630,752 | B2 | 12/2009 | Viswanathan |
| 7,630,753 | B2 | 12/2009 | Simon et al. |
| 7,643,862 | B2 | 1/2010 | Schoenefeld |
| 7,660,623 | B2 | 2/2010 | Hunter et al. |
| 7,661,881 | B2 | 2/2010 | Gregerson et al. |
| 7,683,331 | B2 | 3/2010 | Chang |
| 7,683,332 | B2 | 3/2010 | Chang |
| 7,689,320 | B2 | 3/2010 | Prisco et al. |
| 7,691,098 | B2 | 4/2010 | Wallace et al. |
| 7,702,379 | B2 | 4/2010 | Avinash et al. |
| 7,702,477 | B2 | 4/2010 | Tuemmler et al. |
| 7,711,083 | B2 | 5/2010 | Heigl et al. |
| 7,711,406 | B2 | 5/2010 | Kuhn et al. |
| 7,720,523 | B2 | 5/2010 | Omernick et al. |
| 7,725,253 | B2 | 5/2010 | Foxlin |
| 7,726,171 | B2 | 6/2010 | Langlotz et al. |
| 7,742,801 | B2 | 6/2010 | Neubauer et al. |
| 7,751,865 | B2 | 7/2010 | Jascob et al. |
| 7,760,849 | B2 | 7/2010 | Zhang |
| 7,762,825 | B2 | 7/2010 | Burbank et al. |
| 7,763,015 | B2 | 7/2010 | Cooper et al. |
| 7,787,699 | B2 | 8/2010 | Mahesh et al. |
| 7,796,728 | B2 | 9/2010 | Bergfjord |
| 7,813,838 | B2 | 10/2010 | Sommer |
| 7,818,044 | B2 | 10/2010 | Dukesherer et al. |
| 7,819,859 | B2 | 10/2010 | Prisco et al. |
| 7,824,401 | B2 | 11/2010 | Manzo et al. |
| 7,831,294 | B2 | 11/2010 | Viswanathan |
| 7,834,484 | B2 | 11/2010 | Sartor |
| 7,835,557 | B2 | 11/2010 | Kendrick et al. |
| 7,835,778 | B2 | 11/2010 | Foley et al. |
| 7,835,784 | B2 | 11/2010 | Mire et al. |

(56) References Cited

U.S. PATENT DOCUMENTS 7,840,253 B2 11/2010 Tremblay et al.
7,840,256 B2 11/2010 Lakin et al.
7,843,158 B2 11/2010 Prisco
7,844,320 B2 11/2010 Shahidi
7,853,305 B2 12/2010 Simon et al.
7,853,313 B2 12/2010 Thompson
7,865,269 B2 1/2011 Prisco et al.
D631,966 S 2/2011 Perloff et al.
7,879,045 B2 2/2011 Gielen et al.
7,881,767 B2 2/2011 Strommer et al.
7,881,770 B2 2/2011 Melkent et al.
7,886,743 B2 2/2011 Cooper et al.
RE42,194 E 3/2011 Foley et al.
RE42,226 E 3/2011 Foley et al.
7,900,524 B2 3/2011 Calloway et al.
7,907,166 B2 3/2011 Lamprecht et al.
7,909,122 B2 3/2011 Schena et al.
7,925,653 B2 4/2011 Saptharishi
7,930,065 B2 4/2011 Larkin et al.
7,935,130 B2 5/2011 Willliams
7,940,999 B2 5/2011 Liao et al.
7,945,012 B2 5/2011 Ye et al.
7,945,021 B2 5/2011 Shapiro et al.
7,953,470 B2 5/2011 Vetter et al.
7,954,397 B2 6/2011 Choi et al.
7,971,341 B2 7/2011 Dukesherer et al.
7,974,674 B2 7/2011 Hauck et al.
7,974,677 B2 7/2011 Mire et al.
7,974,681 B2 7/2011 Wallace et al.
7,979,157 B2 7/2011 Anvari
7,983,733 B2 7/2011 Viswanathan
7,988,215 B2 8/2011 Seibold
7,996,110 B2 8/2011 Lipow et al.
8,004,121 B2 8/2011 Sartor
8,004,229 B2 8/2011 Nowlin et al.
8,010,177 B2 8/2011 Csavoy et al.
8,019,045 B2 9/2011 Kato
8,021,310 B2 9/2011 Sanborn et al.
8,035,685 B2 10/2011 Jensen
8,046,054 B2 10/2011 Kim et al.
8,046,057 B2 10/2011 Clarke
8,052,688 B2 11/2011 Wolf, II
8,054,184 B2 11/2011 Cline et al.
8,054,752 B2 11/2011 Druke et al.
8,057,397 B2 11/2011 Li et al.
8,057,407 B2 11/2011 Martinelli et al.
8,062,288 B2 11/2011 Cooper et al.
8,062,375 B2 11/2011 Glerum et al.
8,066,524 B2 11/2011 Burbank et al.
8,073,335 B2 12/2011 Labonville et al.
8,079,950 B2 12/2011 Stern et al.
8,086,299 B2 12/2011 Adler et al.
8,092,370 B2 1/2012 Roberts et al.
8,098,914 B2 1/2012 Liao et al.
8,100,950 B2 1/2012 St. Clair et al.
8,105,320 B2 1/2012 Manzo
8,108,025 B2 1/2012 Csavoy et al.
8,109,877 B2 2/2012 Moctezuma de la Barrera et al.
8,112,292 B2 2/2012 Simon
8,116,430 B1 2/2012 Shapiro et al.
8,120,301 B2 2/2012 Goldberg et al.
8,121,249 B2 2/2012 Wang et al.
8,123,675 B2 2/2012 Funda et al.
8,133,229 B1 3/2012 Bonutti
8,142,420 B2 3/2012 Schena
8,147,494 B2 4/2012 Leitner et al.
8,150,494 B2 4/2012 Simon et al.
8,150,497 B2 4/2012 Gielen et al.
8,150,498 B2 4/2012 Gielen et al.
8,165,658 B2 4/2012 Waynik et al.
8,170,313 B2 5/2012 Kendrick et al.
8,179,073 B2 5/2012 Farritor et al.
8,182,476 B2 5/2012 Julian et al.
8,184,880 B2 5/2012 Zhao et al.
8,202,278 B2 6/2012 Orban, III et al.
8,208,708 B2 6/2012 Homan et al.
8,208,988 B2 6/2012 Jensen
8,219,177 B2 7/2012 Smith et al.
8,219,178 B2 7/2012 Smith et al.
8,220,468 B2 7/2012 Cooper et al.
8,224,024 B2 7/2012 Foxlin et al.
8,224,484 B2 7/2012 Swarup et al.
8,225,798 B2 7/2012 Baldwin et al.
8,228,368 B2 7/2012 Zhao et al.
8,231,610 B2 7/2012 Jo et al.
8,239,001 B2 8/2012 Verard et al.
8,241,271 B2 8/2012 Millman et al.
8,248,413 B2 8/2012 Gattani et al.
8,256,319 B2 9/2012 Cooper et al.
8,263,933 B2 9/2012 Zeile
8,271,069 B2 9/2012 Jascob et al.
8,271,130 B2 9/2012 Hourtash
8,281,670 B2 10/2012 Larkin et al.
8,282,653 B2 10/2012 Nelson et al.
8,301,226 B2 10/2012 Csavoy et al.
8,311,611 B2 11/2012 Csavoy et al.
8,320,991 B2 11/2012 Jascob et al.
8,332,012 B2 12/2012 Kienzle, III
8,333,755 B2 12/2012 Cooper et al.
8,335,552 B2 12/2012 Stiles
8,335,557 B2 12/2012 Maschke
8,348,931 B2 1/2013 Cooper et al.
8,353,963 B2 1/2013 Glerum
8,358,818 B2 1/2013 Miga et al.
8,359,730 B2 1/2013 Burg et al.
8,374,673 B2 2/2013 Adcox et al.
8,374,723 B2 2/2013 Zhao et al.
8,379,791 B2 2/2013 Forthmann et al.
8,386,019 B2 2/2013 Camus et al.
8,392,022 B2 3/2013 Ortmaier et al.
8,394,099 B2 3/2013 Patwardhan
8,395,342 B2 3/2013 Prisco
8,398,634 B2 3/2013 Manzo et al.
8,400,094 B2 3/2013 Schena
8,414,957 B2 4/2013 Enzerink et al.
8,418,073 B2 4/2013 Mohr et al.
8,450,694 B2 5/2013 Baviera et al.
8,452,447 B2 5/2013 Nixon
RE44,305 E 6/2013 Foley et al.
8,462,911 B2 6/2013 Vesel et al.
8,465,476 B2 6/2013 Rogers et al.
8,465,771 B2 6/2013 Wan et al.
8,467,851 B2 6/2013 Mire et al.
8,467,852 B2 6/2013 Csavoy et al.
8,469,947 B2 6/2013 Devengenzo et al.
RE44,392 E 7/2013 Hynes
8,483,434 B2 7/2013 Buehner et al.
8,483,800 B2 7/2013 Jensen et al.
8,486,532 B2 7/2013 Enzerink et al.
8,489,235 B2 7/2013 Moll et al.
8,500,722 B2 8/2013 Cooper
8,500,728 B2 8/2013 Newton et al.
8,504,201 B2 8/2013 Moll et al.
8,506,555 B2 8/2013 Ruiz Morales
8,506,556 B2 8/2013 Schena
8,508,173 B2 8/2013 Goldberg et al.
8,512,318 B2 8/2013 Tovey et al.
8,515,576 B2 8/2013 Lipow et al.
8,518,120 B2 8/2013 Glerum et al.
8,521,331 B2 8/2013 Itkowitz
8,526,688 B2 9/2013 Groszmann et al.
8,526,700 B2 9/2013 Isaacs
8,527,094 B2 9/2013 Kumar et al.
8,528,440 B2 9/2013 Morley et al.
8,532,741 B2 9/2013 Heruth et al.
8,541,970 B2 9/2013 Nowlin et al.
8,548,563 B2 10/2013 Simon et al.
8,549,732 B2 10/2013 Burg et al.
8,551,114 B2 10/2013 Ramos de la Pena
8,551,116 B2 10/2013 Julian et al.
8,556,807 B2 10/2013 Scott et al.
8,556,979 B2 10/2013 Glerum et al.
8,560,118 B2 10/2013 Green et al.
8,561,473 B2 10/2013 Blumenkranz

(56) References Cited

U.S. PATENT DOCUMENTS

| | | | |
|---|---|---|---|
| 8,562,594 | B2 | 10/2013 | Cooper et al. |
| 8,571,638 | B2 | 10/2013 | Shoham |
| 8,571,710 | B2 | 10/2013 | Coste-Maniere et al. |
| 8,573,465 | B2 | 11/2013 | Shelton, IV |
| 8,574,303 | B2 | 11/2013 | Sharkey et al. |
| 8,585,420 | B2 | 11/2013 | Burbank et al. |
| 8,594,841 | B2 | 11/2013 | Zhao et al. |
| 8,597,198 | B2 | 12/2013 | Sanborn et al. |
| 8,600,478 | B2 | 12/2013 | Verard et al. |
| 8,603,077 | B2 | 12/2013 | Cooper et al. |
| 8,611,985 | B2 | 12/2013 | Lavallee et al. |
| 8,613,230 | B2 | 12/2013 | Blumenkranz et al. |
| 8,621,939 | B2 | 1/2014 | Blumenkranz et al. |
| 8,624,537 | B2 | 1/2014 | Nowlin et al. |
| 8,630,389 | B2 | 1/2014 | Kato |
| 8,634,897 | B2 | 1/2014 | Simon et al. |
| 8,634,957 | B2 | 1/2014 | Toth et al. |
| 8,638,056 | B2 | 1/2014 | Goldberg et al. |
| 8,638,057 | B2 | 1/2014 | Goldberg et al. |
| 8,639,000 | B2 | 1/2014 | Zhao et al. |
| 8,641,726 | B2 | 2/2014 | Bonutti |
| 8,644,907 | B2 | 2/2014 | Hartmann et al. |
| 8,657,809 | B2 | 2/2014 | Schoepp |
| 8,660,635 | B2 | 2/2014 | Simon et al. |
| 8,666,544 | B2 | 3/2014 | Moll et al. |
| 8,675,939 | B2 | 3/2014 | Moctezuma de la Barrera |
| 8,678,647 | B2 | 3/2014 | Gregerson et al. |
| 8,679,125 | B2 | 3/2014 | Smith et al. |
| 8,679,183 | B2 | 3/2014 | Glerum et al. |
| 8,682,413 | B2 | 3/2014 | Lloyd |
| 8,684,253 | B2 | 4/2014 | Giordano et al. |
| 8,685,098 | B2 | 4/2014 | Glerum et al. |
| 8,693,730 | B2 | 4/2014 | Umasuthan et al. |
| 8,694,075 | B2 | 4/2014 | Groszmann et al. |
| 8,696,458 | B2 | 4/2014 | Foxlin et al. |
| 8,700,123 | B2 | 4/2014 | Okamura et al. |
| 8,706,086 | B2 | 4/2014 | Glerum |
| 8,706,185 | B2 | 4/2014 | Foley et al. |
| 8,706,301 | B2 | 4/2014 | Zhao et al. |
| 8,717,430 | B2 | 5/2014 | Simon et al. |
| 8,727,618 | B2 | 5/2014 | Maschke et al. |
| 8,734,432 | B2 | 5/2014 | Tuma et al. |
| 8,738,115 | B2 | 5/2014 | Amberg et al. |
| 8,738,181 | B2 | 5/2014 | Greer et al. |
| 8,740,882 | B2 | 6/2014 | Jun et al. |
| 8,746,252 | B2 | 6/2014 | McGrogan et al. |
| 8,749,189 | B2 | 6/2014 | Nowlin et al. |
| 8,749,190 | B2 | 6/2014 | Nowlin et al. |
| 8,761,930 | B2 | 6/2014 | Nixon |
| 8,764,448 | B2 | 7/2014 | Yang et al. |
| 8,771,170 | B2 | 7/2014 | Mesallum et al. |
| 8,781,186 | B2 | 7/2014 | Clements et al. |
| 8,781,630 | B2 | 7/2014 | Banks et al. |
| 8,784,385 | B2 | 7/2014 | Boyden et al. |
| 8,786,241 | B2 | 7/2014 | Nowlin et al. |
| 8,787,520 | B2 | 7/2014 | Baba |
| 8,792,704 | B2 | 7/2014 | Isaacs |
| 8,798,231 | B2 | 8/2014 | Notohara et al. |
| 8,800,838 | B2 | 8/2014 | Shelton, IV |
| 8,808,164 | B2 | 8/2014 | Hoffman et al. |
| 8,812,077 | B2 | 8/2014 | Dempsey |
| 8,814,793 | B2 | 8/2014 | Brabrand |
| 8,816,628 | B2 | 8/2014 | Nowlin et al. |
| 8,818,105 | B2 | 8/2014 | Myronenko et al. |
| 8,820,605 | B2 | 9/2014 | Shelton, IV |
| 8,821,511 | B2 | 9/2014 | Von Jako et al. |
| 8,823,308 | B2 | 9/2014 | Nowlin et al. |
| 8,827,996 | B2 | 9/2014 | Scott et al. |
| 8,828,024 | B2 | 9/2014 | Farritor et al. |
| 8,830,224 | B2 | 9/2014 | Zhao et al. |
| 8,834,489 | B2 | 9/2014 | Cooper et al. |
| 8,834,490 | B2 | 9/2014 | Bonutti |
| 8,838,270 | B2 | 9/2014 | Druke et al. |
| 8,844,789 | B2 | 9/2014 | Shelton, IV et al. |
| 8,855,822 | B2 | 10/2014 | Bartol et al. |
| 8,858,598 | B2 | 10/2014 | Seifert et al. |
| 8,860,753 | B2 | 10/2014 | Bhandarkar et al. |
| 8,864,751 | B2 | 10/2014 | Prisco et al. |
| 8,864,798 | B2 | 10/2014 | Weiman et al. |
| 8,864,833 | B2 | 10/2014 | Glerum et al. |
| 8,867,703 | B2 | 10/2014 | Shapiro et al. |
| 8,870,880 | B2 | 10/2014 | Himmelberger et al. |
| 8,876,866 | B2 | 11/2014 | Zappacosta et al. |
| 8,880,223 | B2 | 11/2014 | Raj et al. |
| 8,882,803 | B2 | 11/2014 | Iott et al. |
| 8,883,210 | B1 | 11/2014 | Truncale et al. |
| 8,888,821 | B2 | 11/2014 | Rezach et al. |
| 8,888,853 | B2 | 11/2014 | Glerum et al. |
| 8,888,854 | B2 | 11/2014 | Glerum et al. |
| 8,894,652 | B2 | 11/2014 | Seifert et al. |
| 8,894,688 | B2 | 11/2014 | Suh |
| 8,894,691 | B2 | 11/2014 | Iott et al. |
| 8,906,069 | B2 | 12/2014 | Hansell et al. |
| 8,964,934 | B2 | 2/2015 | Ein-Gal |
| 8,992,580 | B2 | 3/2015 | Bar et al. |
| 8,996,169 | B2 | 3/2015 | Lightcap et al. |
| 9,001,963 | B2 | 4/2015 | Sowards-Emmerd et al. |
| 9,002,076 | B2 | 4/2015 | Khadem et al. |
| 9,044,190 | B2 | 6/2015 | Rubner et al. |
| 9,107,683 | B2 | 8/2015 | Hourtash et al. |
| 9,125,556 | B2 | 9/2015 | Zehavi et al. |
| 9,131,986 | B2 | 9/2015 | Greer et al. |
| 9,215,968 | B2 | 12/2015 | Schostek et al. |
| 9,308,050 | B2 | 4/2016 | Kostrzewski et al. |
| 9,380,984 | B2 | 7/2016 | Li et al. |
| 9,393,039 | B2 | 7/2016 | Lechner et al. |
| 9,398,886 | B2 | 7/2016 | Gregerson et al. |
| 9,398,890 | B2 | 7/2016 | Dong et al. |
| 9,414,859 | B2 | 8/2016 | Ballard et al. |
| 9,420,975 | B2 | 8/2016 | Gutfleisch et al. |
| 9,492,235 | B2 | 11/2016 | Hourtash et al. |
| 9,592,096 | B2 | 3/2017 | Maillet et al. |
| 9,750,465 | B2 | 9/2017 | Engel et al. |
| 9,757,203 | B2 | 9/2017 | Hourtash et al. |
| 9,795,354 | B2 | 10/2017 | Menegaz et al. |
| 9,814,535 | B2 | 11/2017 | Bar et al. |
| 9,820,783 | B2 | 11/2017 | Donner et al. |
| 9,833,265 | B2 | 12/2017 | Donner et al. |
| 9,848,922 | B2 | 12/2017 | Tohmeh et al. |
| 9,925,011 | B2 | 3/2018 | Gombert et al. |
| 9,931,025 | B1 | 4/2018 | Graetzel et al. |
| 10,034,717 | B2 | 7/2018 | Miller et al. |
| 2001/0036302 | A1 | 11/2001 | Miller |
| 2002/0035321 | A1 | 3/2002 | Bucholz et al. |
| 2004/0068172 | A1 | 4/2004 | Nowinski et al. |
| 2004/0076259 | A1 | 4/2004 | Jensen et al. |
| 2005/0096502 | A1 | 5/2005 | Khalili |
| 2005/0143651 | A1 | 6/2005 | Verard et al. |
| 2005/0171558 | A1 | 8/2005 | Abovitz et al. |
| 2006/0100610 | A1 | 5/2006 | Wallace et al. |
| 2006/0173329 | A1 | 8/2006 | Marquart et al. |
| 2006/0184396 | A1 | 8/2006 | Dennis et al. |
| 2006/0241416 | A1 | 10/2006 | Marquart et al. |
| 2006/0291612 | A1 | 12/2006 | Nishide et al. |
| 2007/0015987 | A1 | 1/2007 | Benlloch Baviera et al. |
| 2007/0021738 | A1 | 1/2007 | Hasser et al. |
| 2007/0038059 | A1 | 2/2007 | Sheffer et al. |
| 2007/0073133 | A1 | 3/2007 | Schoenefeld |
| 2007/0156121 | A1 | 7/2007 | Millman et al. |
| 2007/0156157 | A1 | 7/2007 | Nahum et al. |
| 2007/0167712 | A1 | 7/2007 | Keglovich et al. |
| 2007/0233238 | A1 | 10/2007 | Huynh et al. |
| 2008/0004523 | A1 | 1/2008 | Jensen |
| 2008/0013809 | A1 | 1/2008 | Zhu et al. |
| 2008/0033283 | A1 | 2/2008 | Dellaca et al. |
| 2008/0046122 | A1 | 2/2008 | Manzo et al. |
| 2008/0082109 | A1 | 4/2008 | Moll et al. |
| 2008/0108912 | A1 | 5/2008 | Node-Langlois |
| 2008/0108991 | A1 | 5/2008 | Von Jako |
| 2008/0109012 | A1 | 5/2008 | Falco et al. |
| 2008/0144906 | A1 | 6/2008 | Allred et al. |
| 2008/0161680 | A1 | 7/2008 | Von Jako et al. |
| 2008/0161682 | A1 | 7/2008 | Kendrick et al. |
| 2008/0177203 | A1 | 7/2008 | von Jako |

(56) References Cited

U.S. PATENT DOCUMENTS

| | | | |
|---|---|---|---|
| 2008/0214922 | A1 | 9/2008 | Hartmann et al. |
| 2008/0228068 | A1 | 9/2008 | Viswanathan et al. |
| 2008/0228196 | A1 | 9/2008 | Wang et al. |
| 2008/0235052 | A1 | 9/2008 | Node-Langlois et al. |
| 2008/0269596 | A1 | 10/2008 | Revie et al. |
| 2008/0287771 | A1 | 11/2008 | Anderson |
| 2008/0287781 | A1 | 11/2008 | Revie et al. |
| 2008/0300477 | A1 | 12/2008 | Lloyd et al. |
| 2008/0300478 | A1 | 12/2008 | Zuhars et al. |
| 2008/0302950 | A1 | 12/2008 | Park et al. |
| 2008/0306490 | A1 | 12/2008 | Lakin et al. |
| 2008/0319311 | A1 | 12/2008 | Hamadeh |
| 2009/0012509 | A1 | 1/2009 | Csavoy et al. |
| 2009/0030428 | A1 | 1/2009 | Omori et al. |
| 2009/0080737 | A1 | 3/2009 | Battle et al. |
| 2009/0185655 | A1 | 7/2009 | Koken et al. |
| 2009/0198121 | A1 | 8/2009 | Hoheisel |
| 2009/0216113 | A1 | 8/2009 | Meier et al. |
| 2009/0228019 | A1 | 9/2009 | Gross et al. |
| 2009/0259123 | A1 | 10/2009 | Navab et al. |
| 2009/0259230 | A1 | 10/2009 | Khadem et al. |
| 2009/0264899 | A1 | 10/2009 | Appenrodt et al. |
| 2009/0281417 | A1 | 11/2009 | Hartmann et al. |
| 2010/0022874 | A1 | 1/2010 | Wang et al. |
| 2010/0039506 | A1 | 2/2010 | Sarvestani et al. |
| 2010/0125286 | A1 | 5/2010 | Wang et al. |
| 2010/0130986 | A1 | 5/2010 | Mailloux et al. |
| 2010/0228117 | A1 | 9/2010 | Hartmann |
| 2010/0228265 | A1 | 9/2010 | Prisco |
| 2010/0249571 | A1 | 9/2010 | Jensen et al. |
| 2010/0274120 | A1 | 10/2010 | Heuscher |
| 2010/0280363 | A1 | 11/2010 | Skarda et al. |
| 2010/0331858 | A1 | 12/2010 | Simaan et al. |
| 2011/0022229 | A1 | 1/2011 | Jang et al. |
| 2011/0077504 | A1 | 3/2011 | Fischer et al. |
| 2011/0098553 | A1 | 4/2011 | Robbins et al. |
| 2011/0137152 | A1 | 6/2011 | Li |
| 2011/0213384 | A1 | 9/2011 | Jeong |
| 2011/0224684 | A1 | 9/2011 | Larkin et al. |
| 2011/0224685 | A1 | 9/2011 | Larkin et al. |
| 2011/0224686 | A1 | 9/2011 | Larkin et al. |
| 2011/0224687 | A1 | 9/2011 | Larkin et al. |
| 2011/0224688 | A1 | 9/2011 | Larkin et al. |
| 2011/0224689 | A1 | 9/2011 | Larkin et al. |
| 2011/0224825 | A1 | 9/2011 | Larkin et al. |
| 2011/0230967 | A1 | 9/2011 | O'Halloran et al. |
| 2011/0238080 | A1 | 9/2011 | Ranjit et al. |
| 2011/0276058 | A1 | 11/2011 | Choi et al. |
| 2011/0282189 | A1 | 11/2011 | Graumann |
| 2011/0286573 | A1 | 11/2011 | Schretter et al. |
| 2011/0295062 | A1 | 12/2011 | Gratacos Solsona et al. |
| 2011/0295370 | A1 | 12/2011 | Suh et al. |
| 2011/0306986 | A1 | 12/2011 | Lee et al. |
| 2012/0035507 | A1 | 2/2012 | George et al. |
| 2012/0046668 | A1 | 2/2012 | Gantes |
| 2012/0051498 | A1 | 3/2012 | Koishi |
| 2012/0053597 | A1 | 3/2012 | Anvari et al. |
| 2012/0059248 | A1 | 3/2012 | Holsing et al. |
| 2012/0071753 | A1 | 3/2012 | Hunter et al. |
| 2012/0108954 | A1 | 5/2012 | Schulhauser et al. |
| 2012/0136372 | A1 | 5/2012 | Amat Girbau et al. |
| 2012/0143084 | A1 | 6/2012 | Shoham |
| 2012/0184839 | A1 | 7/2012 | Woerlein |
| 2012/0197182 | A1 | 8/2012 | Millman et al. |
| 2012/0226145 | A1 | 9/2012 | Chang et al. |
| 2012/0235909 | A1 | 9/2012 | Birkenbach et al. |
| 2012/0245596 | A1 | 9/2012 | Meenink |
| 2012/0253332 | A1 | 10/2012 | Moll |
| 2012/0253360 | A1 | 10/2012 | White et al. |
| 2012/0256092 | A1 | 10/2012 | Zingerman |
| 2012/0294498 | A1 | 11/2012 | Popovic |
| 2012/0296203 | A1 | 11/2012 | Hartmann et al. |
| 2013/0006267 | A1 | 1/2013 | Odermatt et al. |
| 2013/0016889 | A1 | 1/2013 | Myronenko et al. |
| 2013/0030571 | A1 | 1/2013 | Ruiz Morales et al. |
| 2013/0035583 | A1 | 2/2013 | Park et al. |
| 2013/0060146 | A1 | 3/2013 | Yang et al. |
| 2013/0060337 | A1 | 3/2013 | Petersheim et al. |
| 2013/0094742 | A1 | 4/2013 | Feilkas |
| 2013/0096574 | A1 | 4/2013 | Kang et al. |
| 2013/0113791 | A1 | 5/2013 | Isaacs et al. |
| 2013/0116706 | A1 | 5/2013 | Lee et al. |
| 2013/0131695 | A1 | 5/2013 | Scarfogliero et al. |
| 2013/0144307 | A1 | 6/2013 | Jeong et al. |
| 2013/0158542 | A1 | 6/2013 | Manzo et al. |
| 2013/0165937 | A1 | 6/2013 | Patwardhan |
| 2013/0178867 | A1 | 7/2013 | Farritor et al. |
| 2013/0178868 | A1 | 7/2013 | Roh |
| 2013/0178870 | A1 | 7/2013 | Schena |
| 2013/0204271 | A1 | 8/2013 | Brisson et al. |
| 2013/0211419 | A1 | 8/2013 | Jensen |
| 2013/0211420 | A1 | 8/2013 | Jensen |
| 2013/0218142 | A1 | 8/2013 | Tuma et al. |
| 2013/0223702 | A1 | 8/2013 | Holsing et al. |
| 2013/0225942 | A1 | 8/2013 | Holsing et al. |
| 2013/0225943 | A1 | 8/2013 | Holsing et al. |
| 2013/0231556 | A1 | 9/2013 | Holsing et al. |
| 2013/0237995 | A1 | 9/2013 | Lee et al. |
| 2013/0245375 | A1 | 9/2013 | DiMaio et al. |
| 2013/0261640 | A1 | 10/2013 | Kim et al. |
| 2013/0272488 | A1 | 10/2013 | Bailey et al. |
| 2013/0272489 | A1 | 10/2013 | Dickman et al. |
| 2013/0274761 | A1 | 10/2013 | Devengenzo et al. |
| 2013/0281821 | A1 | 10/2013 | Liu et al. |
| 2013/0296884 | A1 | 11/2013 | Taylor et al. |
| 2013/0303887 | A1 | 11/2013 | Holsing et al. |
| 2013/0307955 | A1 | 11/2013 | Deitz et al. |
| 2013/0317521 | A1 | 11/2013 | Choi et al. |
| 2013/0325033 | A1 | 12/2013 | Schena et al. |
| 2013/0325035 | A1 | 12/2013 | Hauck et al. |
| 2013/0331686 | A1 | 12/2013 | Freysinger et al. |
| 2013/0331858 | A1 | 12/2013 | Devengenzo et al. |
| 2013/0331861 | A1 | 12/2013 | Yoon |
| 2013/0342578 | A1 | 12/2013 | Isaacs |
| 2013/0345717 | A1 | 12/2013 | Markvicka et al. |
| 2013/0345757 | A1 | 12/2013 | Stad |
| 2014/0001235 | A1 | 1/2014 | Shelton, IV |
| 2014/0012131 | A1 | 1/2014 | Heruth et al. |
| 2014/0031664 | A1 | 1/2014 | Kang et al. |
| 2014/0046128 | A1 | 2/2014 | Lee et al. |
| 2014/0046132 | A1 | 2/2014 | Hoeg et al. |
| 2014/0046340 | A1 | 2/2014 | Wilson et al. |
| 2014/0049629 | A1 | 2/2014 | Siewerdsen et al. |
| 2014/0058406 | A1 | 2/2014 | Tsekos |
| 2014/0073914 | A1 | 3/2014 | Lavallee et al. |
| 2014/0080086 | A1 | 3/2014 | Chen |
| 2014/0081128 | A1 | 3/2014 | Verard et al. |
| 2014/0088612 | A1 | 3/2014 | Bartol et al. |
| 2014/0094694 | A1 | 4/2014 | Moctezuma de la Barrera |
| 2014/0094851 | A1 | 4/2014 | Gordon |
| 2014/0096369 | A1 | 4/2014 | Matsumoto et al. |
| 2014/0100587 | A1 | 4/2014 | Farritor et al. |
| 2014/0121676 | A1 | 5/2014 | Kostrzewski et al. |
| 2014/0128882 | A1 | 5/2014 | Kwak et al. |
| 2014/0130810 | A1 | 5/2014 | Azizian et al. |
| 2014/0135796 | A1 | 5/2014 | Simon et al. |
| 2014/0142591 | A1 | 5/2014 | Alvarez et al. |
| 2014/0142592 | A1 | 5/2014 | Moon et al. |
| 2014/0148692 | A1 | 5/2014 | Hartmann et al. |
| 2014/0163581 | A1 | 6/2014 | Devengenzo et al. |
| 2014/0171781 | A1 | 6/2014 | Stiles |
| 2014/0171900 | A1 | 6/2014 | Stiles |
| 2014/0171965 | A1 | 6/2014 | Loh et al. |
| 2014/0180308 | A1 | 6/2014 | von Grunberg |
| 2014/0180309 | A1 | 6/2014 | Seeber et al. |
| 2014/0187915 | A1 | 7/2014 | Yaroshenko et al. |
| 2014/0188132 | A1 | 7/2014 | Kang |
| 2014/0194699 | A1 | 7/2014 | Roh et al. |
| 2014/0221819 | A1 | 8/2014 | Sarment |
| 2014/0222023 | A1 | 8/2014 | Kim et al. |
| 2014/0228631 | A1 | 8/2014 | Kwak et al. |
| 2014/0234804 | A1 | 8/2014 | Huang et al. |
| 2014/0257328 | A1 | 9/2014 | Kim et al. |
| 2014/0257329 | A1 | 9/2014 | Jang et al. |

(56) References Cited

U.S. PATENT DOCUMENTS

| | | | |
|---|---|---|---|
| 2014/0257330 | A1 | 9/2014 | Choi et al. |
| 2014/0275760 | A1 | 9/2014 | Lee et al. |
| 2014/0275985 | A1 | 9/2014 | Walker et al. |
| 2014/0276931 | A1 | 9/2014 | Parihar et al. |
| 2014/0276940 | A1 | 9/2014 | Seo |
| 2014/0276944 | A1 | 9/2014 | Farritor et al. |
| 2014/0288413 | A1 | 9/2014 | Hwang et al. |
| 2014/0299648 | A1 | 10/2014 | Shelton, IV et al. |
| 2014/0303434 | A1 | 10/2014 | Farritor et al. |
| 2014/0303643 | A1 | 10/2014 | Ha et al. |
| 2014/0305995 | A1 | 10/2014 | Shelton, IV et al. |
| 2014/0309659 | A1 | 10/2014 | Roh et al. |
| 2014/0316436 | A1 | 10/2014 | Bar et al. |
| 2014/0323803 | A1 | 10/2014 | Hoffman et al. |
| 2014/0324070 | A1 | 10/2014 | Min et al. |
| 2014/0330288 | A1 | 11/2014 | Date et al. |
| 2014/0364720 | A1 | 12/2014 | Darrow et al. |
| 2014/0371577 | A1 | 12/2014 | Maillet et al. |
| 2015/0039034 | A1 | 2/2015 | Frankel et al. |
| 2015/0085970 | A1 | 3/2015 | Bouhnik et al. |
| 2015/0146847 | A1 | 5/2015 | Liu |
| 2015/0150524 | A1 | 6/2015 | Yorkston et al. |
| 2015/0196261 | A1 | 7/2015 | Funk |
| 2015/0213633 | A1 | 7/2015 | Chang et al. |
| 2015/0335480 | A1 | 11/2015 | Alvarez et al. |
| 2015/0342647 | A1 | 12/2015 | Frankel et al. |
| 2016/0005194 | A1 | 1/2016 | Schretter et al. |
| 2016/0166329 | A1 | 6/2016 | Langan et al. |
| 2016/0235480 | A1 | 8/2016 | Scholl et al. |
| 2016/0249990 | A1 | 9/2016 | Glozman et al. |
| 2016/0302871 | A1 | 10/2016 | Gregerson et al. |
| 2016/0320322 | A1 | 11/2016 | Suzuki |
| 2016/0331335 | A1 | 11/2016 | Gregerson et al. |
| 2017/0135770 | A1 | 5/2017 | Scholl et al. |
| 2017/0143284 | A1 | 5/2017 | Sehnert et al. |
| 2017/0143426 | A1 | 5/2017 | Isaacs et al. |
| 2017/0156816 | A1 | 6/2017 | Ibrahim |
| 2017/0202629 | A1 | 7/2017 | Maillet et al. |
| 2017/0212723 | A1 | 7/2017 | Atarot et al. |
| 2017/0215825 | A1 | 8/2017 | Johnson et al. |
| 2017/0215826 | A1 | 8/2017 | Johnson et al. |
| 2017/0215827 | A1 | 8/2017 | Johnson et al. |
| 2017/0231710 | A1 | 8/2017 | Scholl et al. |
| 2017/0258426 | A1 | 9/2017 | Risher-Kelly et al. |
| 2017/0273748 | A1 | 9/2017 | Hourtash et al. |
| 2017/0296277 | A1 | 10/2017 | Hourtash et al. |
| 2017/0360493 | A1 | 12/2017 | Zucher et al. |
| 2019/0060556 | A1* | 2/2019 | Huiszoon .............. A61M 5/001 |
| 2024/0148328 | A1* | 5/2024 | Fedon .................. A61B 5/0538 |

OTHER PUBLICATIONS

V. Makarovaite, etc. "Passive UHF RFID Voice Prosthesis Mounted Sensor for Microbial Growth Detection," in IEEE Journal of Radio Frequency Identification, vol. 4, No. 4, pp. 384-390, Dec. 2020 (Year: 2020).*

* cited by examiner

IMPLANTABLE RF SENSOR FOR BIOFILM DETECTION

CROSS-REFERENCE TO RELATED APPLICATIONS

The present application is a continuation of U.S. patent application Ser. No. 18/477,841, filed on Sep. 29, 2023, which is incorporated herein by reference.

FIELD

The present disclosure relates to medical implants, including joint arthroplasty.

BACKGROUND

Periprosthetic joint infection (PJI) is one of the most feared complications in joint arthroplasty due to the ineffectiveness of antibiotics, invasive treatment options, and relatively high annual mortality rate of 4%. If caught early enough, antibiotics and natural immune responses are very effective at intercepting the free-floating bacteria within the surgical site. However, antibiotics are remarkably ineffective at eradicating bacteria within biofilm on the surface of the implant.

Biofilm develops as bacteria adhere to and colonize on the surface of an implant. The biofilm layer serves as a biochemical fortress that prevents penetration of antibiotic agents. It has been reported that 500-5000 times the concentration of antibiotics are required to have the same effectiveness on biofilm bacteria as compared to free-floating planktonic bacteria. As a result, the most common treatment for PJI is highly invasive two-stage revision.

Two-stage revision involves an initial operation to remove the septic implant and debride the surgical site and a second procedure to place new implant components. Although two-stage revision is the most common treatment option for PJI, the success rate has been reported to be only 85%. In addition, the risk of reinfection following revision for PJI has been reported to be 9% compared to 1-2% following the primary procedure. Also, the annual mortality rate has been reported to be as high as 14% following two-stage revision.

SUMMARY

Embodiments of the present disclosure are directed to smart joint reconstruction implants that can provide physicians/clinicians and their patients the ability to monitor, detect, and diagnose PJI.

Some embodiments of the present disclosure are directed to a medical implant that includes an implant component configured to be implanted in a patient, a radio frequency (RF) transmit antenna in the implant component and configured to transmit a RF signal, and circuitry within the implant component. The circuitry is operative to generate the RF signal to the RF transmit antenna, determine a characteristic of attenuation of the RF signal when the RF transmit antenna is transmitting the RF signal while implanted in the patient, and detect presence of biofilm on the medical implant based on the characteristic of attenuation of the RF signal.

Possible advantages that may be provided by one or one of these and other embodiments disclosed herein may include early monitoring of a formation of biofilm to provide early detection of PJI and feedback on the effectiveness of treatment. Additionally, the embodiment(s) may provide sensing and/or control elements integrated within the tibial insert. These sensing and/or control elements may provide the benefit(s) of no additional components on the surface of the implant exposed to synovial fluid and tissue and greater reliability.

Other medical implants and corresponding methods according to embodiments of the present disclosure will be or become apparent to one with skill in the art upon review of the following drawings and detailed description. It is intended that all such additional medical implants and methods be included within this description, be within the scope of the present inventive subject matter, and be protected by the accompanying claims. Moreover, it is intended that all embodiments disclosed herein can be implemented separately or combined in any way and/or combination.

DESCRIPTION OF THE DRAWINGS

Aspects of the present disclosure are illustrated by way of example and are not limited by the accompanying drawings. In the drawings.

DETAILED DESCRIPTION

Figure 1:
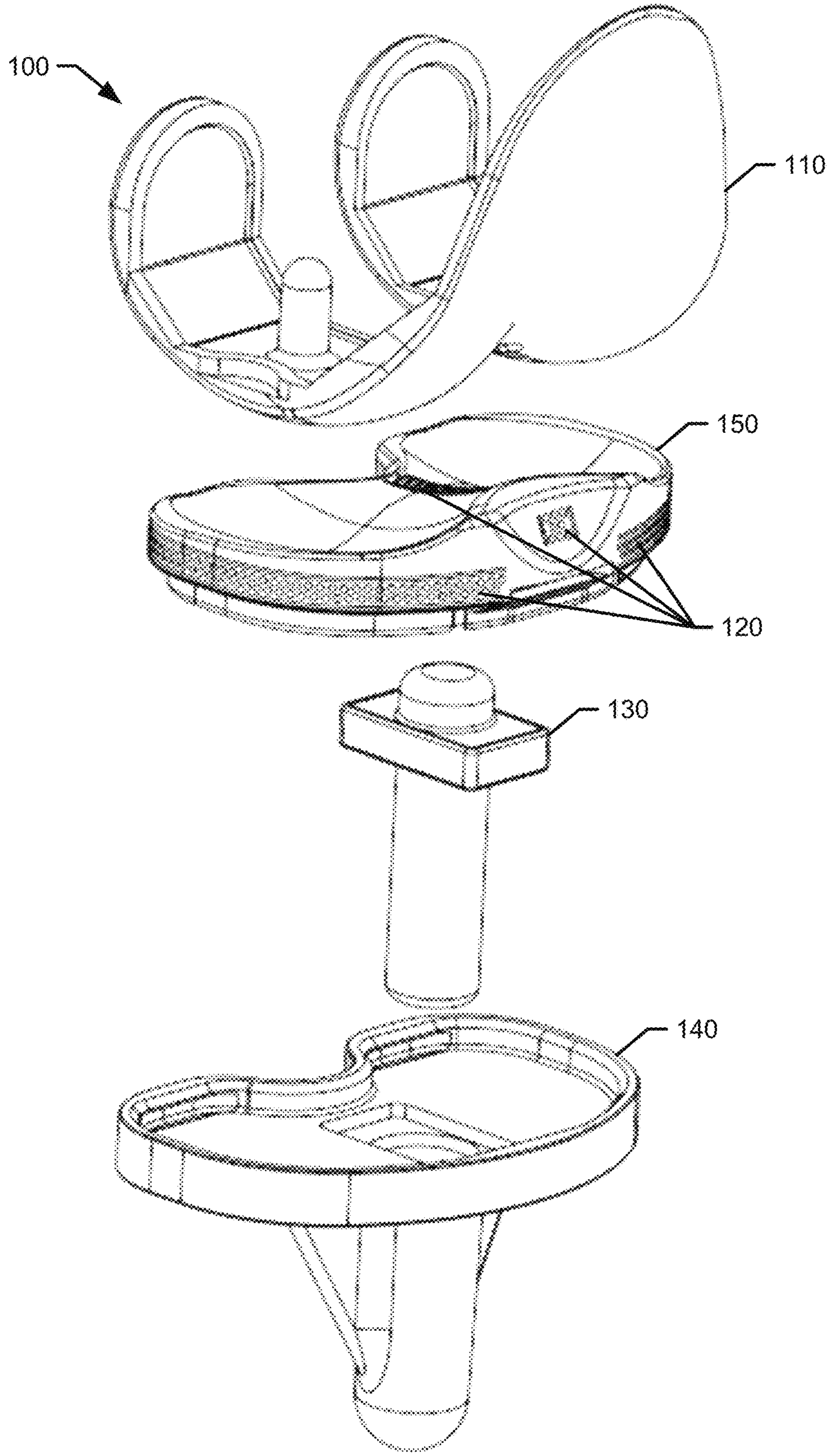
FIG. 1 illustrates an exploded isometric view of some components of a medical implant including a femoral component, tibial insert, energy storage device, and tibial tray according to some embodiments of the present disclosure.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Some embodiments of the present disclosure are directed to joint reconstruction implants that have electronic circuits ("smart implants") which operate to provide physicians and/or their patients the operational ability to monitor, detect, and diagnose Periprosthetic Joint Infection (PJI). The smart implant may include an implantable RF sensor (e.g., a RF antenna) capable of detecting bacterial biofilm on the surface of implant components.

Post-operatively, the smart implant may sense the presence of biofilm on the surface of implant components and transmit the sensor readings to a clinician. The clinician may decide on treatment based on the sensor readings, information provided to the clinician through an accompanying patient engagement mobile app, and direct consultation. If the clinician determines that the patient has developed or is likely to develop an infection, they may more closely monitor the patient and intervene with antibiotics or surgical debridement.

FIG. 1 illustrates an exploded isometric view of some components of a medical implant 100 including a femoral component 110, tibial insert 150, energy storage device 130, and tibial tray 140 according to some embodiments of the present disclosure.

Referring to FIG. 1, medical implant 100 is a knee replacement implant. The tibial insert 150 may be housed between the tibial tray 140 and femoral component 110 within cavities in each component. FIG. 1 is an implant construct for total knee arthroplasty, however, it should be noted that the present disclosure is directed to various embodiments in any orthopedic implant application including but not limited to partial knee arthroplasty, revision knee arthroplasty, total hip arthroplasty, intramedullary nailing, trauma plating, and spinal fusion.

The tibial insert 150 of the medical implant 100 may include at least one RF antenna (e.g., plurality of RF antennas 120) that is exposed to or shielded from (e.g., RF window discussed below) fluid and/or tissue of a patient that the medical implant 100 is implanted in. For example, the tibial insert 150 includes two sets of RF antennas in sides of the tibial insert 150, a third set of RF antennas in a top of the tibial insert 150 that is facing upward, and a fourth set of RF antennas that is in a front of the tibial insert 150 and is facing in a tilted forward facing direction. While embodiments illustrate and describe specific placements of the one or more RF antennas, embodiments herein are not limited to such placements and can be in any surface of the medical implant 100 such as the tibial insert 150, femoral component 110, and/or tibial tray 140. The femoral component 110, tibial insert 150, and tibial tray 140 may generally be referred to herein as an implant component.

In some preferred embodiments, the RF antennas are placed in locations where there is minimal or no articulating wear from the different components of the medical implant. For example, in locations where the different components of the medical implant do not contact each other while implanted in the patient. However, since the RF antenna(s) are in the medical implant 100 and can be protected by a RF window (discussed more below), the RF antenna(s) may be in locations where this is articular wear from the different components of the medical implant.

In additional or alternative embodiments, the RF antennas are placed in locations where biofilm is more likely to form on the medical implant 100.

Figure 2A:
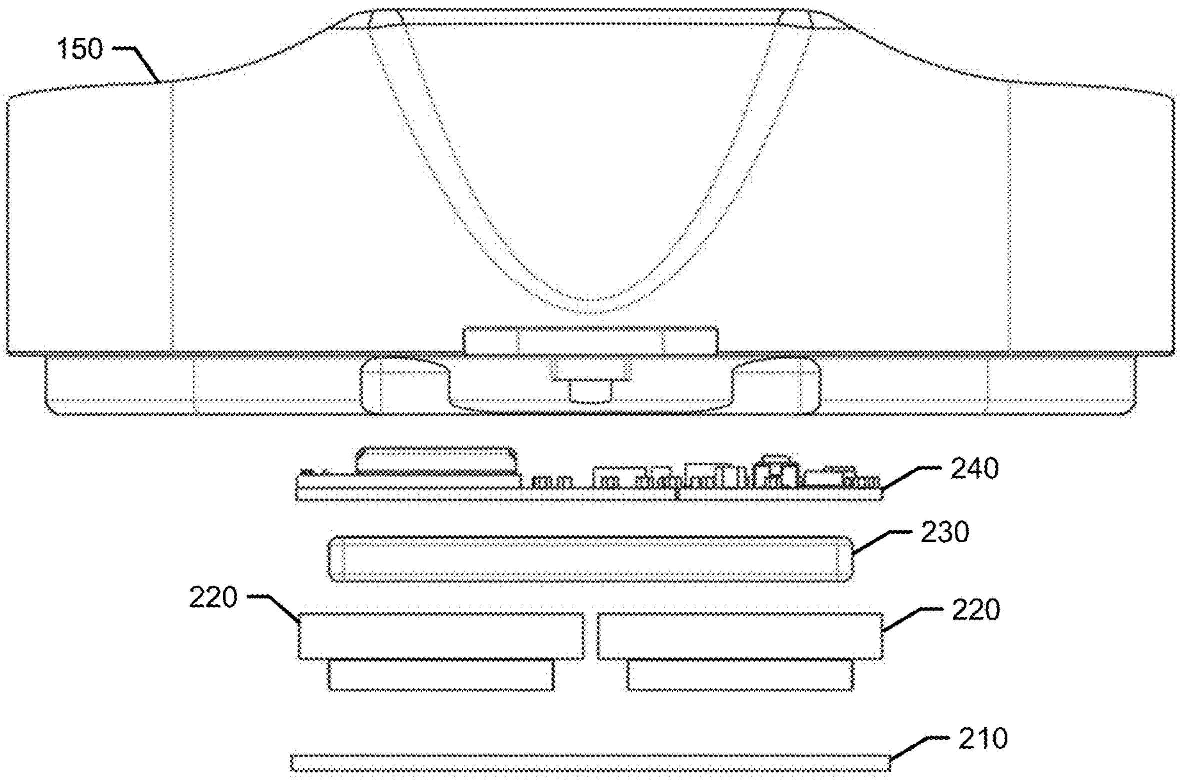
FIG. 2A illustrates a side exploded view of the tibial insert with an integrated RF-based biofilm sensor with laterally spaced transmission (Tx) and reception (Rx) antennas, according to some embodiments of the present disclosure.

FIG. 2A illustrates a side exploded view of the tibial insert 150 with an integrated RF-based biofilm sensor with laterally spaced transmission (Tx) and reception (Rx) antennas (e.g., RF antennas 220 which may include a RF transmit antenna and a RF receive antenna), according to some embodiments of the present disclosure. The term "RF antenna" can correspond to an antenna that is configured to resonate when excited with a transmit/receive signal in a defined RF frequency range.

It should be noted that while one RF transmit antenna and one RF receive antenna is illustrated herein, more than one RF transmit antenna and more than one RF receive antenna may be used. Additionally, in some embodiments, the RF receive antenna is optional as will be below.

In some embodiments, sets of RF transmit antennas and RF receive antennas are located in different locations in the medical implant and are used to monitor and detect the presence of biofilm at the corresponding different locations on the medical implant. In some embodiments, the sets comprise one or more RF transmit antennas and one or more RF receive antennas. In additional or alternative embodiments, the sets comprise more than one RF transmit antenna and one RF receive antenna, or vice versa.

Figure 2B:
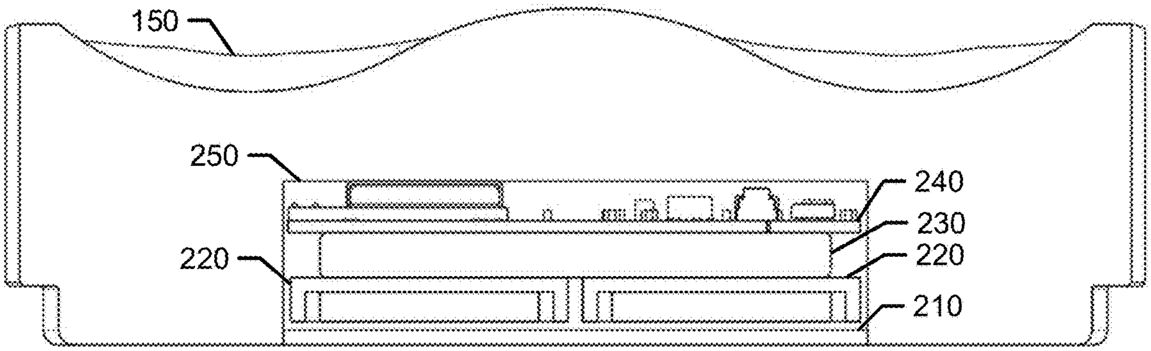
FIG. 2B illustrates a side sectional view of the tibial insert with an integrated RF-based biofilm sensor with laterally spaced Tx and Rx antennas, according to some embodiments of the present disclosure.

FIG. 2B illustrates a side sectional view of the tibial insert 150 with the integrated RF-based biofilm sensor with laterally spaced Tx and Rx antennas (e.g., the RF antennas 220), according to some embodiments of the present disclosure.

The tibial insert 150 may include a RF window 210 that extends across the RF transmit antenna and the RF receive antenna (e.g., RF based antennas 220) and separates the antennas from fluid and/or tissue while the medical implant is implanted in the patient. The RF window 210 may be a layer that comprises the same material or a different material than an adjacent surface of the medical implant. In some embodiments, the RF window 210 and the medical implant comprise of a RF-transparent material. In some embodiments, the RF window 210 hermetically seals the RF based antennas 220 within a housing 250 in the tibial insert 150.

The RF based antennas 220 may be substantially shielded from each other by electromagnetic field (EMF) shielding to reduce or prevent a shortest distance (direct) signal pathway therebetween (discussed in more detail below).

Biofilm typically forms non-uniformly in one or more spots on the surface of the medical implant where planktonic bacterial attachment is preferential due to surface roughness or other factors. In some embodiments, the RF window could be intentionally designed to serve as the preferential attachment surface for planktonic bacteria, thereby increasing the probability that a biofilm forms on the RF window rather than a non-instrumented portion of the medical implant surface. For example, the RF window may include a rougher surface, exposed to the patient (e.g., fluid and/or tissue of the patient), than an adjacent surface of the implant component (e.g., tibial insert 150 of FIG. 2A) exposed to the patient to promote earlier formation of biofilm on the rougher surface of the RF window. Alternatively or additionally, an external surface of the RF window may be covered with a material that promotes earlier formation of biofilm.

The tibial insert 150 further includes an energy storage device 230, e.g., rechargeable battery or capacitive circuitry, that is additional to or alternative of the energy storage device 130. In some embodiments, the energy storage device 230 may be configured to power the circuitry 240 within the tibial insert 150 and/or the RF antennas 220 within the tibial insert 150. In other embodiments, circuitry 240 is powered primarily or fully by the energy storage device 130 of FIG. 1. In embodiments where the energy storage device 130 is the primary source of power, the energy storage device 230 acts as secondary or back-up power source.

Circuitry 240 may include one or more processor circuits ("processor") which execute instructions stored in one or more memory circuits ("memory"), and/or application specific integrated circuit(s) which perform defined logical operations. The circuitry further includes RF amplifier(s) and transmitter circuits, and may include a RF receiver circuits.

In some embodiments, the RF antennas 220 are electrically connected to the energy storage device (e.g., energy storage device 130 and/or energy storage device 230) through insulated electrical traces or wires routed on the surface of the tibial insert 150 or through the body of the tibial insert 150. The electrical traces or wires may terminate at connectors that interface with pass-through connectors of the tibial insert 150. The housing 250 of the tibial insert 150 (along with other parts of the medical implant) may be constructed at least in part of a material that minimizes RF interference. In some embodiment, the top portions of the housing are constructed of a RF transparent material such as PEEK (polyetheretherketone) to allow transmission of the radio waves. In some embodiments, the bottom component of the housing could be constructed of a RF transparent material such as PEEK or a RF shielding material such as TAV (titanium).

In some embodiments, circuitry 240 is a printed circuit assembly (PCA). The PCA may include electronic components and circuitry required for communication, wireless charging, sensing, including the RF antenna(s).

As shown in FIG. 2B, in some embodiments, the RF based antennas 220 (e.g., RF transmit antenna and/or the RF receive antenna), the energy storage device 230, and circuitry 240 are recessed in the implant component (e.g., tibial insert 150). Housing 250 along with the RF window may support these components within the medical implant.

Figure 3A:
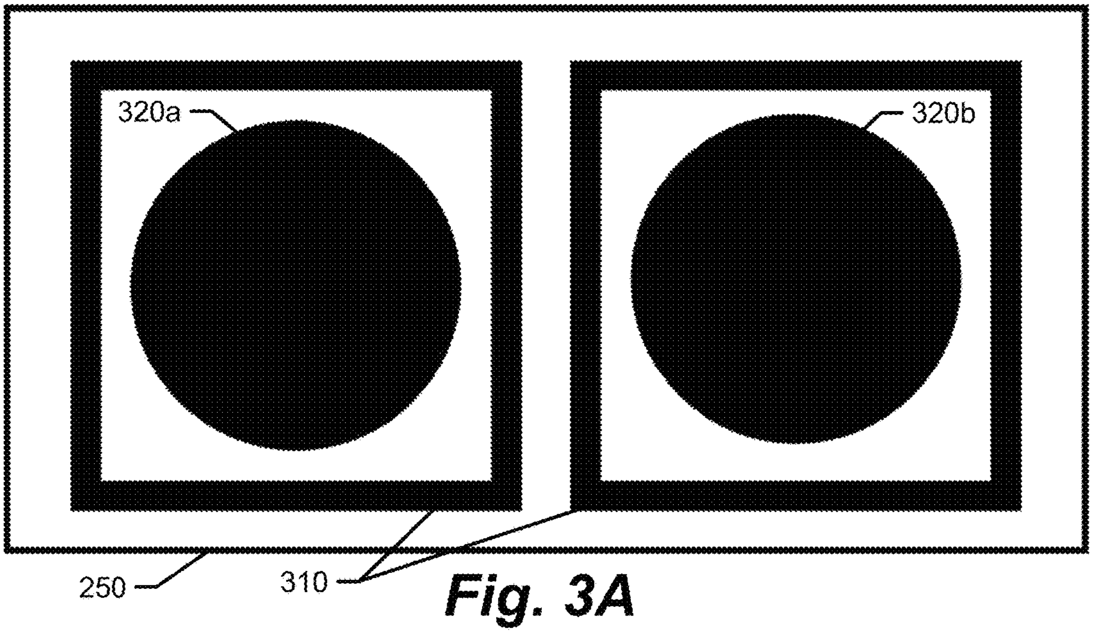
FIG. 3A illustrates a top view of a RF-based biofilm sensor with laterally spaced Tx and Rx antennas, according to some embodiments of the present disclosure.

FIG. 3A illustrates a top view of a RF-based biofilm sensor with laterally spaced Tx and Rx antennas, according to some embodiments of the present disclosure.

The laterally spaced Tx and Rx antennas may include at least one RF transmit antenna 320*a* and at least one RF transmit antenna 320*b*.

The RF transmit antenna 320*a* may be in (at least partially within) the implant component (e.g., a tibial insert 150) and configured to transmit a RF signal. The RF receive antenna 320*b* may be in the implant component (e.g., a tibial insert 150) and configured to receive the RF signal.

The housing 250 of the tibial insert 150 may include EMF shielding 310 positioned between the RF transmit antenna 320*a* and the RF receive antenna 320*b* and configured to attenuate RF signaling along a direct pathway from the RF transmit antenna 320*a* to the RF receive antenna 320*b* through the EMF shielding.

Figure 3B:
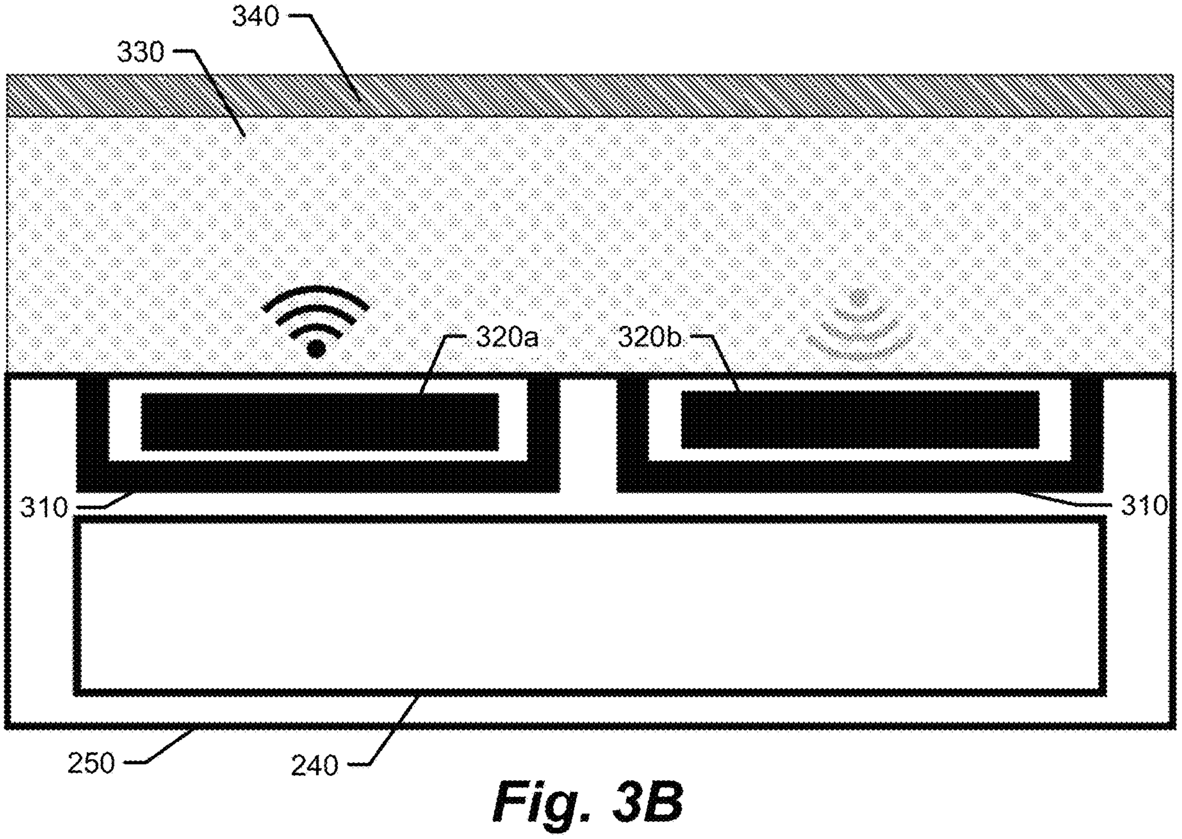
FIG. 3B illustrates a side sectional view of a RF-based biofilm sensor with laterally spaced Tx and Rx antennas, according to some embodiments of the present disclosure.

FIG. 3B illustrates a side sectional view of a RF-based biofilm sensor with laterally spaced Tx and Rx antennas, according to some embodiments of the present disclosure.

In some embodiments, the medical implant includes an implant component (e.g., tibial insert 150) configured to be implanted in a patient, a RF transmit antenna 320*a* in the implant component and configured to transmit a RF signal, and circuitry 240 within the implant component that is operative to generate a RF signal to the RF transmit antenna 320*a*. The circuitry is further operative to determine a characteristic of attenuation of the RF signal when the RF transmit antenna 320*a* is transmitting the RF signal while implanted in the patient. The circuitry is further operative to detect presence of biofilm based on the characteristic of attenuation of the RF signal.

In some embodiments, the characteristic of attenuation of the RF signal is determined based on the reflected power of the RF signal provided by the circuitry 240 toward the RF transmit antenna 320*a*. For these operations, the characteristic of attenuation may be detected without necessarily including a receive antenna and coupled receive circuitry.

In some embodiments, the medical implant further includes a RF receive antenna 320*n* in the implant component and configured to receive the RF signal. In these embodiments, the characteristic of attenuation of the RF signal is determined based on the RF signal characteristics received at the RF receive antenna. The RF signal is transmitted by the RF transmit antenna 320*a* and travels through fluid 330 and/or tissue 340 of the patient and is received by the RF receive antenna 320*b*. Then circuitry 240 determines a characteristic of attenuation of the RF signal based on the RF signal characteristics received at the RF receive antenna.

In some embodiments, the RF transmit antenna 320*a* and the RF receive antenna 320*b* are physically spaced apart from each other along a surface of the medical implant.

In some embodiments, the characteristic of attenuation of the RF signal is determined based on at least one of reflected power of the RF signal provided by the circuitry 240 toward the RF transmit antenna 320*a*, power transferred by the RF signal from the RF transmit antenna 320*a* to a RF receive antenna 320*b* in the implant component (e.g., tibial insert 150) and configured to receive the RF signal, a change in frequency between the RF signal transmitted by the RF transmit antenna 320*a* and the RF signal received by the RF receive antenna 320*b*, and a change in amplitude between the RF signal transmitted by the RF transmit antenna 320*a* and the RF signal received by the RF receive antenna 320*b*, a change in phase between the RF signal transmitted by the RF transmit antenna 320*a* and the RF signal received by the RF receive antenna 320*b*.

Figure 3C:
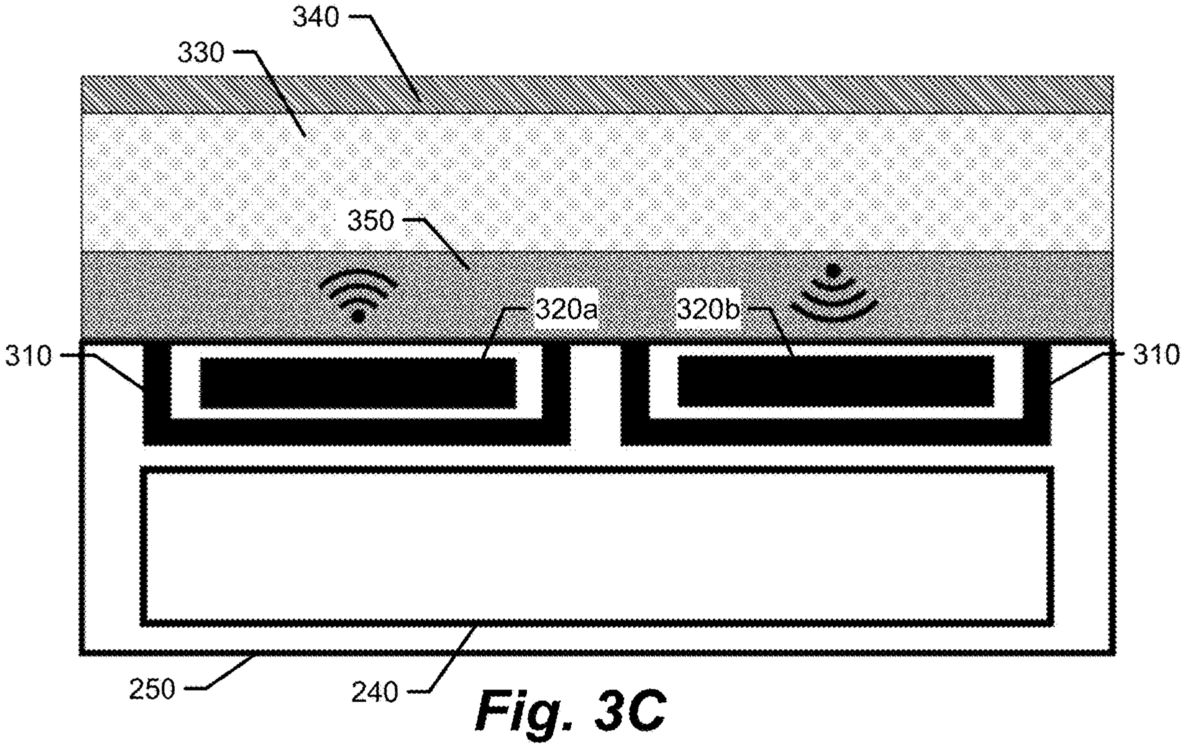
FIG. 3C illustrates a side sectional view of a RF-based biofilm sensor with laterally spaced Tx and Rx antennas according to some embodiments of the present disclosure, and with biofilm present.

FIG. 3C illustrates a side sectional view of a RF-based biofilm sensor with laterally spaced Tx and Rx antennas (e.g., RF transmit antenna 320*a* and RF receive antenna 320*b*) according to some embodiments of the present disclosure, and with biofilm 350 present.

In some embodiments, the detection of the presence of biofilm 350 comprises comparing the determined characteristic of attenuation of the RF signal to a threshold characteristic of attenuation defined based on a calibration measurement operation. For example, the characteristic(s) of attenuation could be compared to previously determined characteristic(s) of attenuation that were measured during a calibration measurement operation that occurred a period of time after the medical implant was implanted into the patient. In preferred embodiments, the calibration measurement operation would occur a short period after implantation into the patient to help ensure that biofilm has not already built up on the medical implant.

In some embodiments, the detection of the presence of biofilm comprises comparing the characteristic of attenuation of the RF signal to at least one prior characteristic of attenuation, and determining that biofilm is present based on the characteristic of attenuation of the RF signal being a threshold difference than the prior characteristic of attenuation. For example, if a characteristic of attenuation is determined to be a threshold difference than a previously determined characteristic of attenuation, then this may indicate the presence of biofilm on the medical implant, likely on a surface of the medical implant near the RF transmit antenna and/or the RF receive antenna.

Figure 3D:
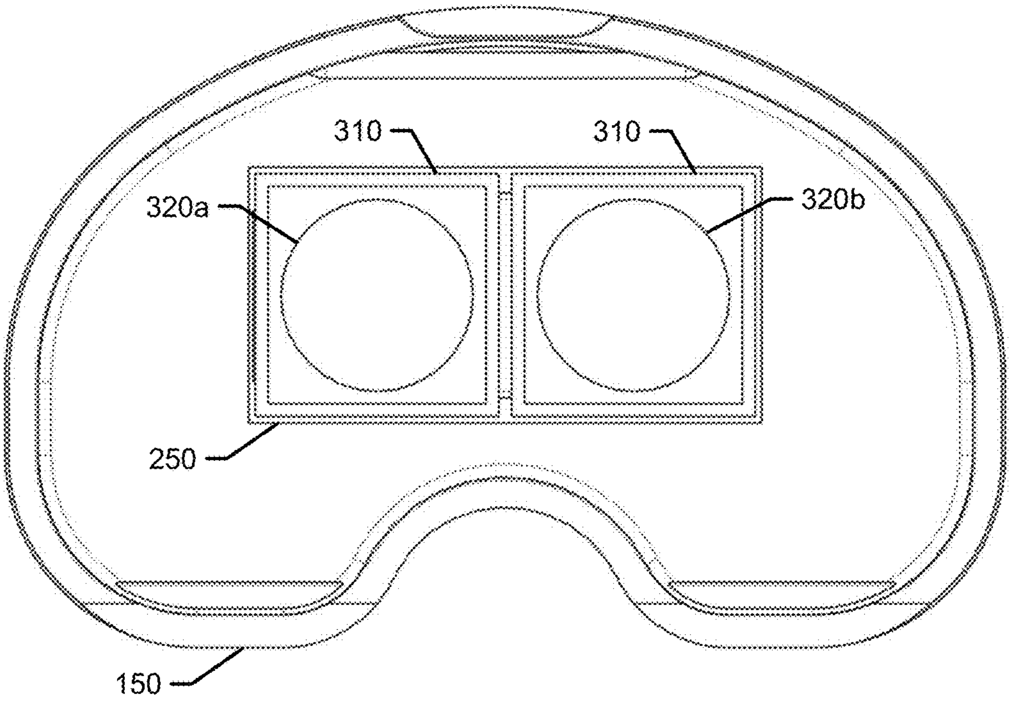
FIG. 3D illustrates a bottom view of the tibial insert with an integrated RF-based biofilm sensor with laterally spaced Tx and Rx antennas, according to some embodiments of the present disclosure.

FIG. 3D illustrates a bottom view of the tibial insert 150 with an integrated RF-based biofilm sensor with laterally spaced Tx and Rx antennas (e.g., RF transmit antenna 320*a* and RF receive antenna 320*b*), according to some embodiments of the present disclosure. In some embodiments, the RF transmit antenna 320*a* transmits signals out of the bottom of the tibial insert 150 to monitor and detect presence of biofilm on the bottom of the tibial insert 150.

Figure 4A:
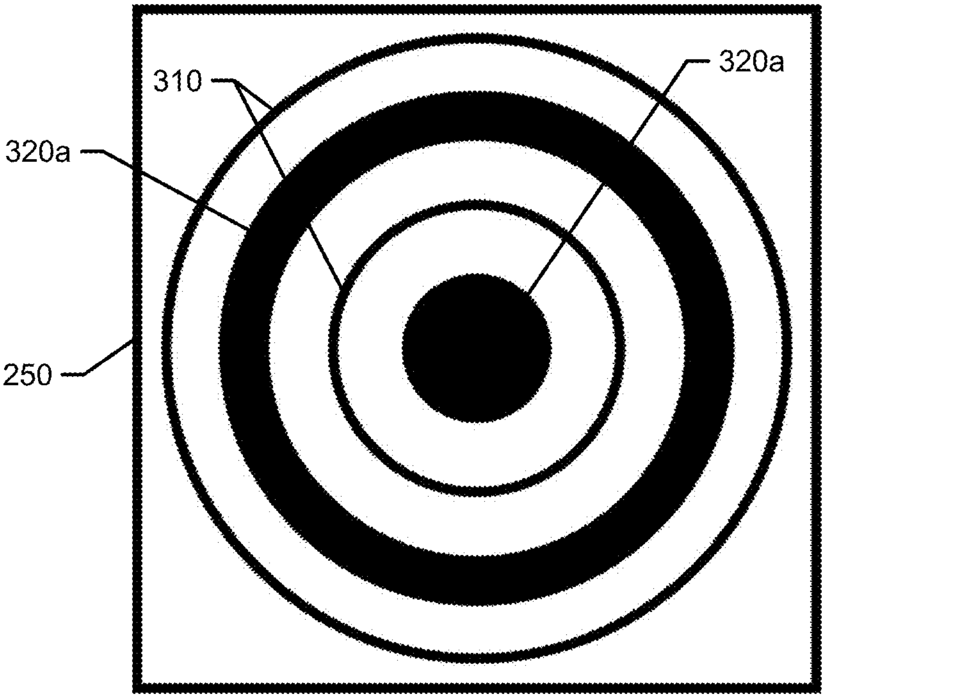
FIG. 4A illustrates a top view of a RF-based biofilm sensor with coaxial Tx and Rx antennas, according to some embodiments of the present disclosure.

FIG. 4A illustrates a top view of a RF-based biofilm sensor with coaxial Tx and Rx antennas (e.g., RF transmit antenna 320*a* and RF receive antenna 320*b*), according to some embodiments of the present disclosure.

In some embodiments, the RF transmit antenna 320*a* and RF receive antenna 320*b* are circular shaped and arranged concentrically with different diameters. For example, the RF transmit antenna 320*a* and RF receive antenna 320*b* may be coaxial and housed within the housing 250 in the tibial insert. In some embodiments, the housing 250 and/or implant component includes EMF shielding 310 positioned between the RF transmit antenna 320*a* and the RF receive antenna 320*b* and configured to attenuate RF signaling along a direct pathway from the RF transmit antenna 320*a* to the RF receive antenna 320*b* through the EMF shielding. The EMF shielding 310 may help to prevent the RF signal from being transmitted directly from the RF transmit antenna 320*a* to the RF receive antenna 320*b*, and may force the RF signal to travel through fluid 330 and or tissue 340 of the patient.

Concentrically is used herein to refer to one antenna being encircled by another antenna but which may or may not be coaxially aligned therewith.

Figure 4B:
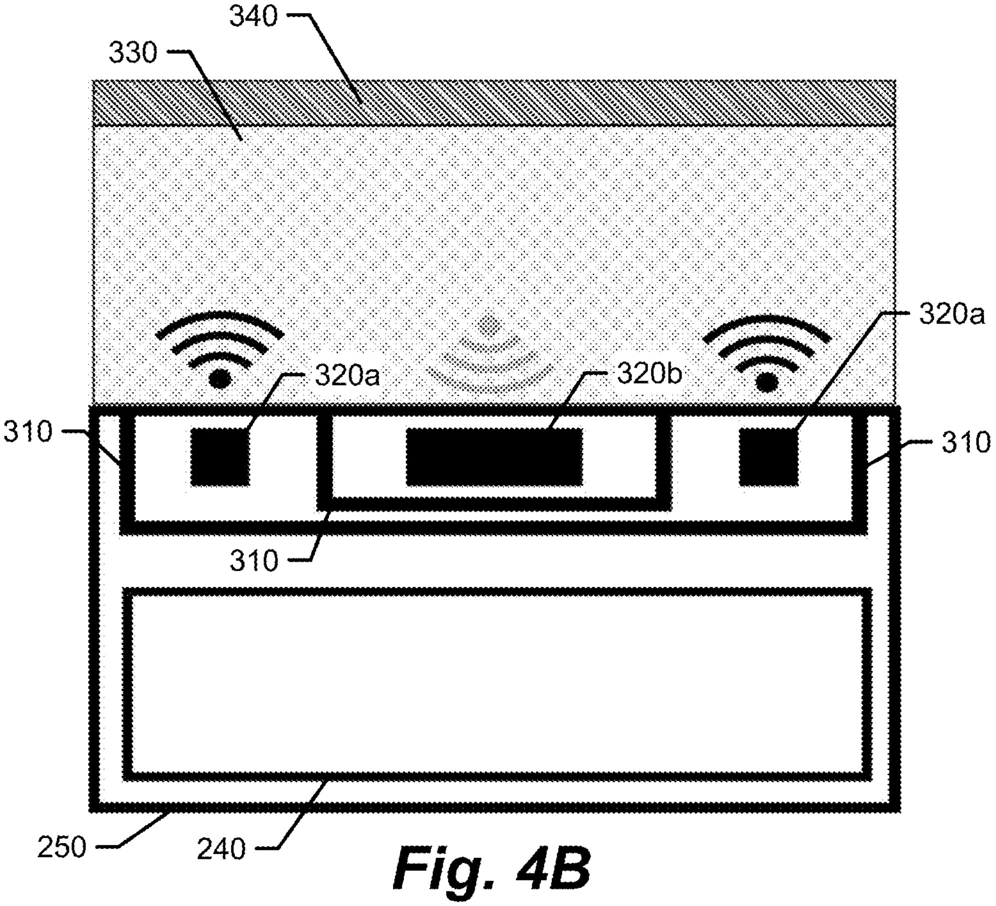
FIG. 4B illustrates a side sectional view of a RF-based biofilm sensor with coaxial Tx and Rx antennas, according to some embodiments of the present disclosure.

FIG. 4B illustrates a side sectional view of a RF-based biofilm sensor with coaxial Tx and Rx antennas (e.g., RF transmit antenna 320*a* and RF receive antenna 320*b*), according to some embodiments of the present disclosure. FIG. 4B is similar to FIG. 3B, except the RF transmit antenna 320*a* and RF receive antenna are circular shaped and arranged concentrically with different diameters. The RF transmit antenna 320*a* may transmit RF signal(s) and the RF receive antenna 320*b* may receive the RF signal(s) after the RF signal travels through fluid 330 and/or tissue 340 of a patient that the medical implant is implanted in.

Figure 4C:
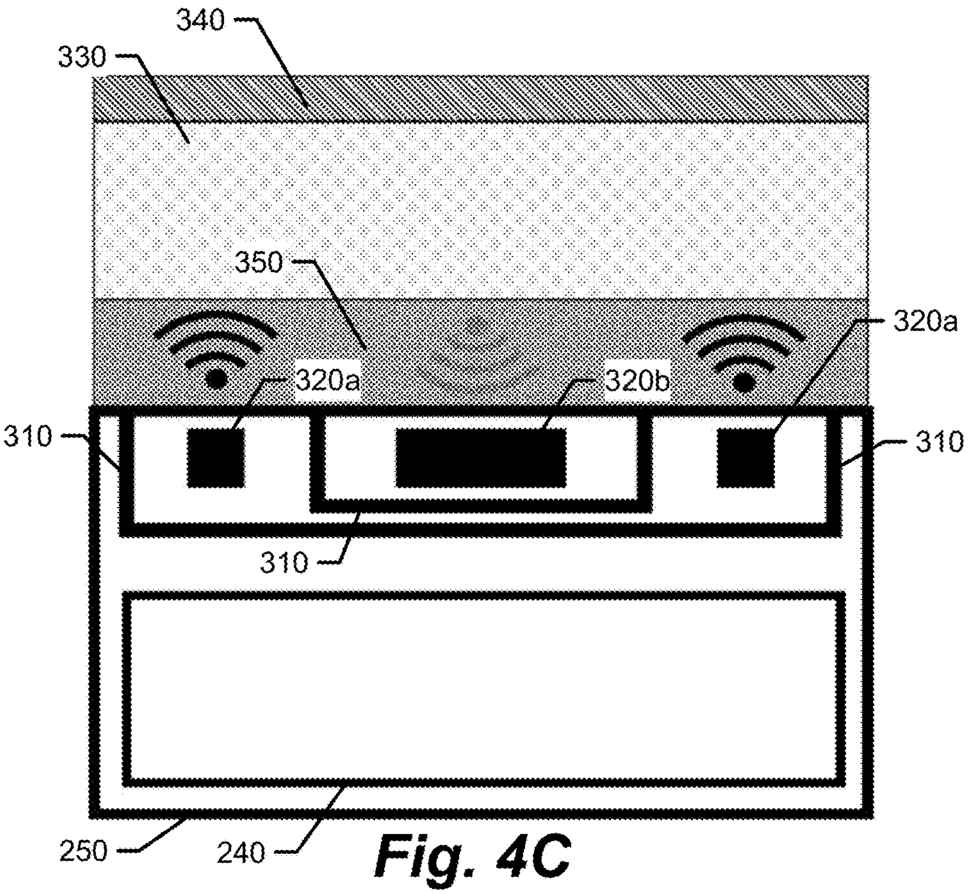
FIG. 4C illustrates a side sectional view of a RF-based biofilm sensor with coaxial Tx and Rx antennas according to some embodiments of the present disclosure, and with biofilm present.

FIG. 4C illustrates a side sectional view of a RF-based biofilm sensor with coaxial Tx and Rx antennas (e.g., RF transmit antenna 320*a* and RF receive antenna 320*b*) according to some embodiments of the present disclosure, and with biofilm present.

Figure 4D:
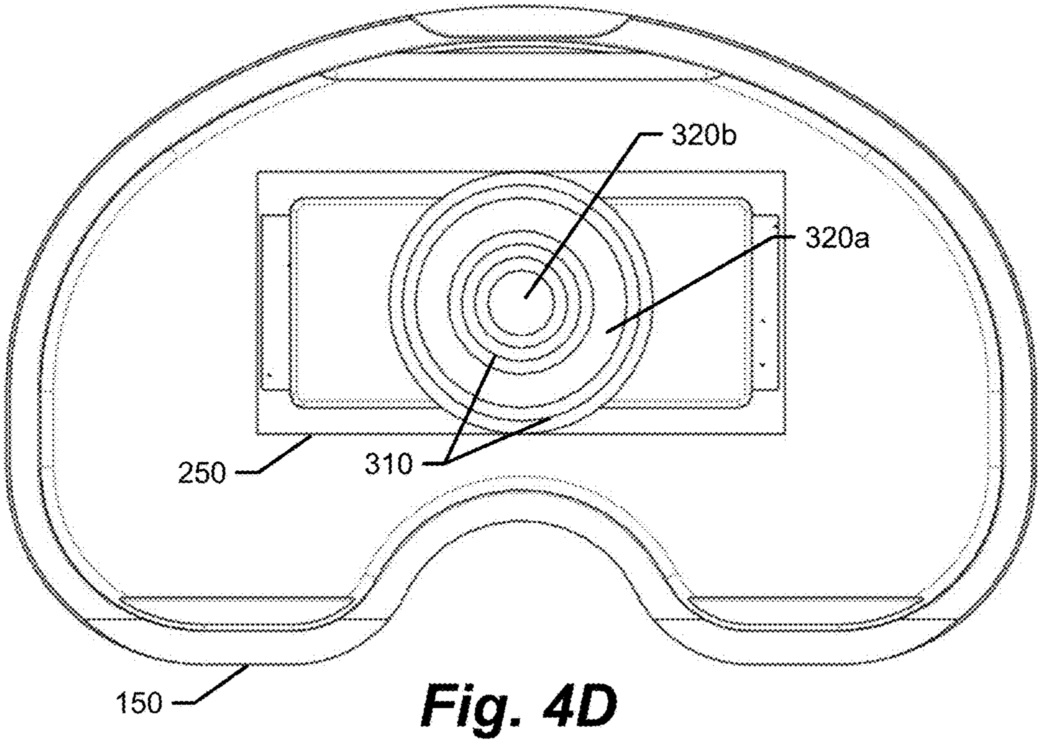
FIG. 4D illustrates a bottom view of the tibial insert with an integrated RF-based biofilm sensor with coaxial Tx and Rx antennas, according to some embodiments of the present disclosure.

FIG. 4D illustrates a bottom view of the tibial insert with an integrated RF-based biofilm sensor with coaxial Tx and Rx antennas, according to some embodiments of the present disclosure.

Figure 5A:
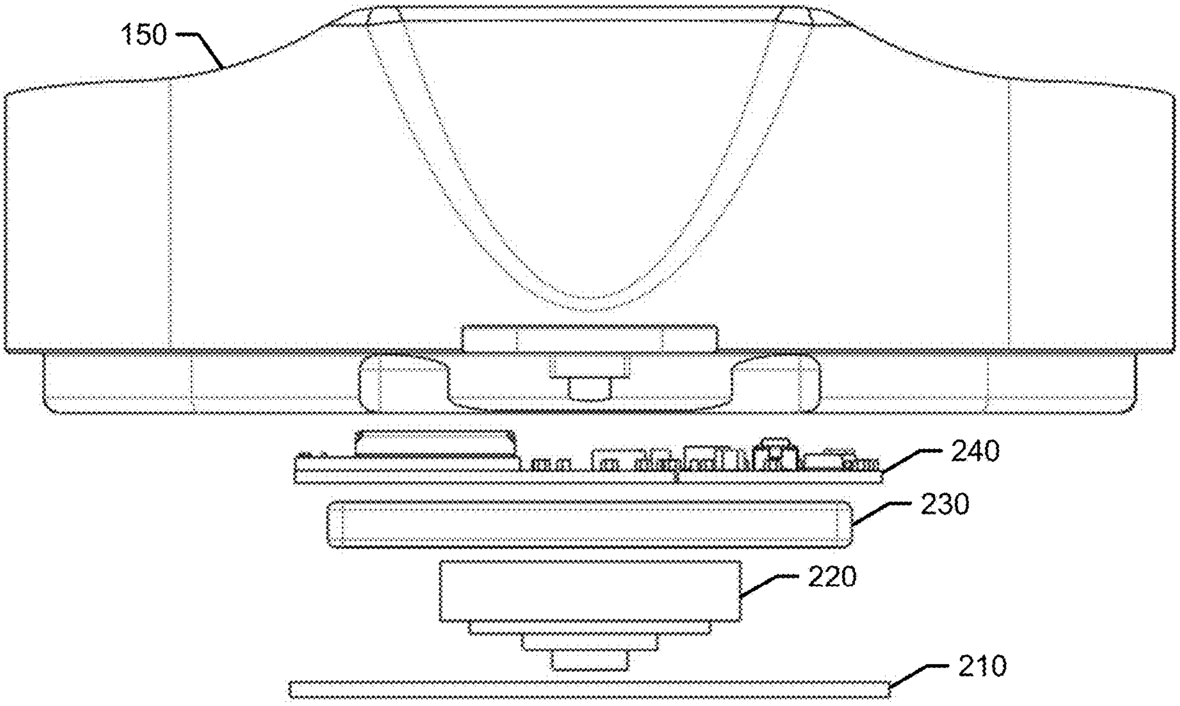
FIG. 5A illustrates a side sectional view of the tibial insert with an integrated RF-based biofilm sensor with coaxial Tx and Rx antennas, according to some embodiments of the present disclosure.

FIG. 5A illustrates a side sectional view of the tibial insert with an integrated RF-based biofilm sensor with coaxial Tx and Rx antennas (e.g., RF based antennas 220), according to some embodiments of the present disclosure.

Figure 5B:
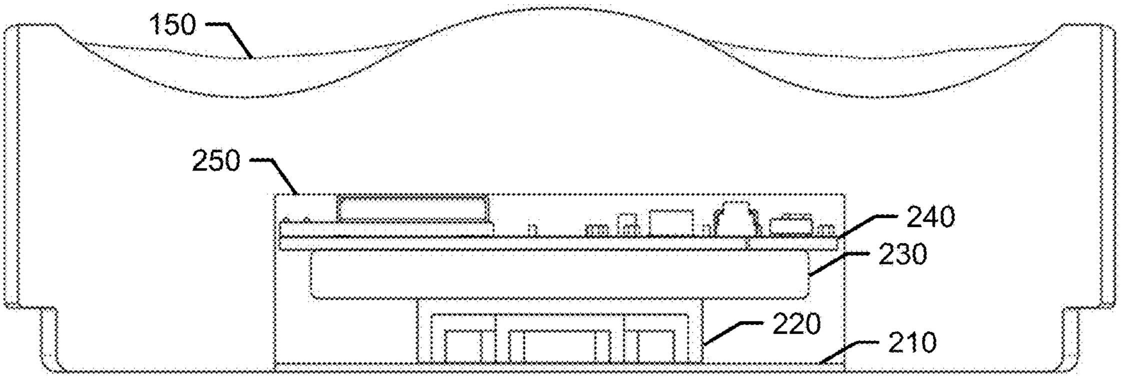
FIG. 5B illustrates a side exploded view of the tibial insert with an integrated RF-based biofilm sensor with coaxial Tx and Rx antennas, according to some embodiments of the present disclosure.

FIG. 5B illustrates a side exploded view of the tibial insert with an integrated RF-based biofilm sensor with coaxial Tx and Rx antennas (e.g., RF based antennas 220), according to some embodiments of the present disclosure.

Figure 6A:
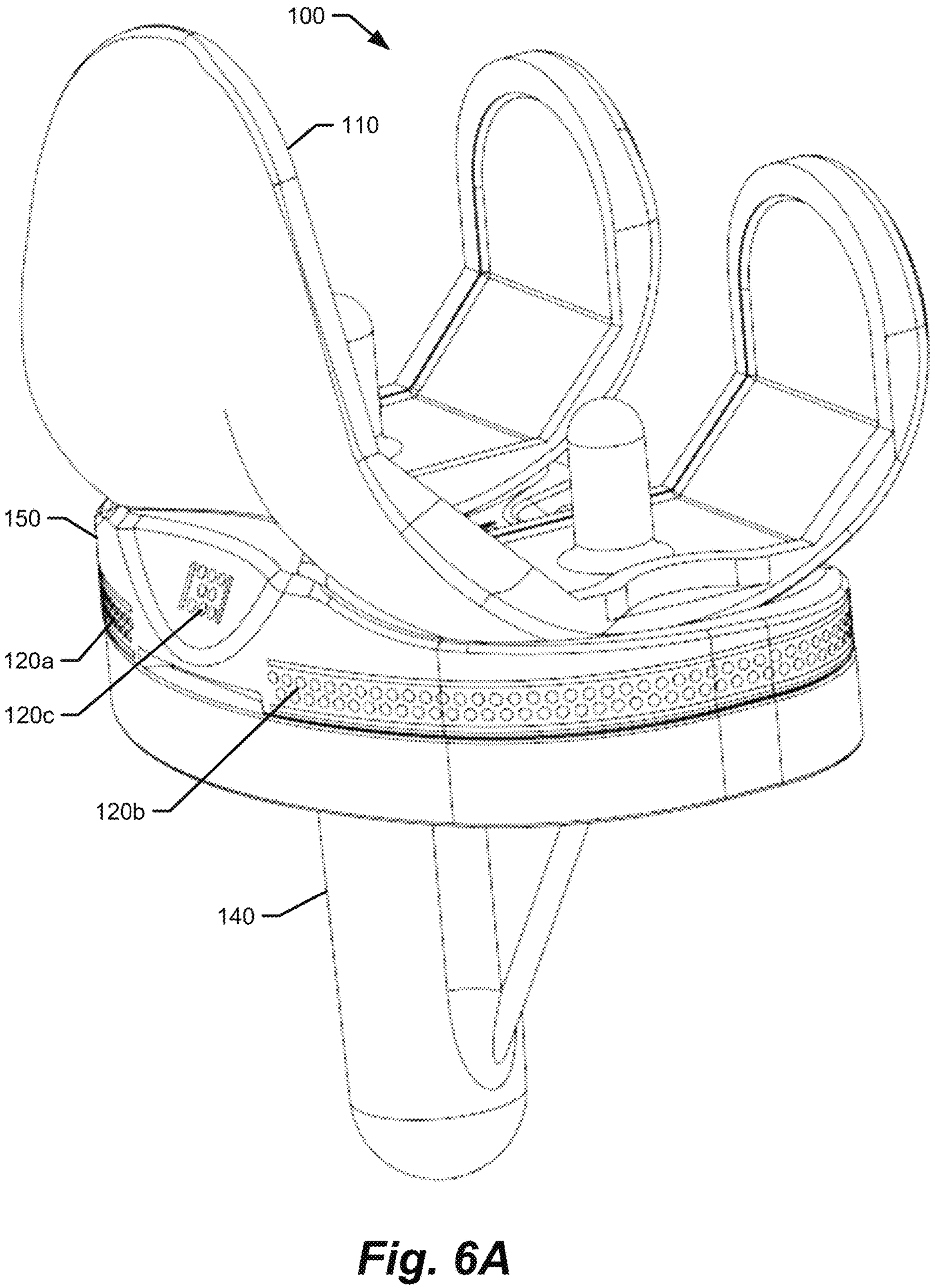
FIG. 6A illustrates another view of the medical implant with sets of RF-based biofilm sensors on either side of the tibial insert and another set of RF-based biofilm sensors centrally located on a frontward face of the tibial insert, according to some embodiments of the present disclosure.

FIG. 6A illustrates another view of the medical implant 100 with sets of RF-based biofilm sensors 120*a*-*b* on either side of the tibial insert 150 and another set of RF-based biofilm sensors 120*c* centrally located on a frontward (sideward) face of the tibial insert 150, according to some embodiments of the present disclosure.

Figure 6B:
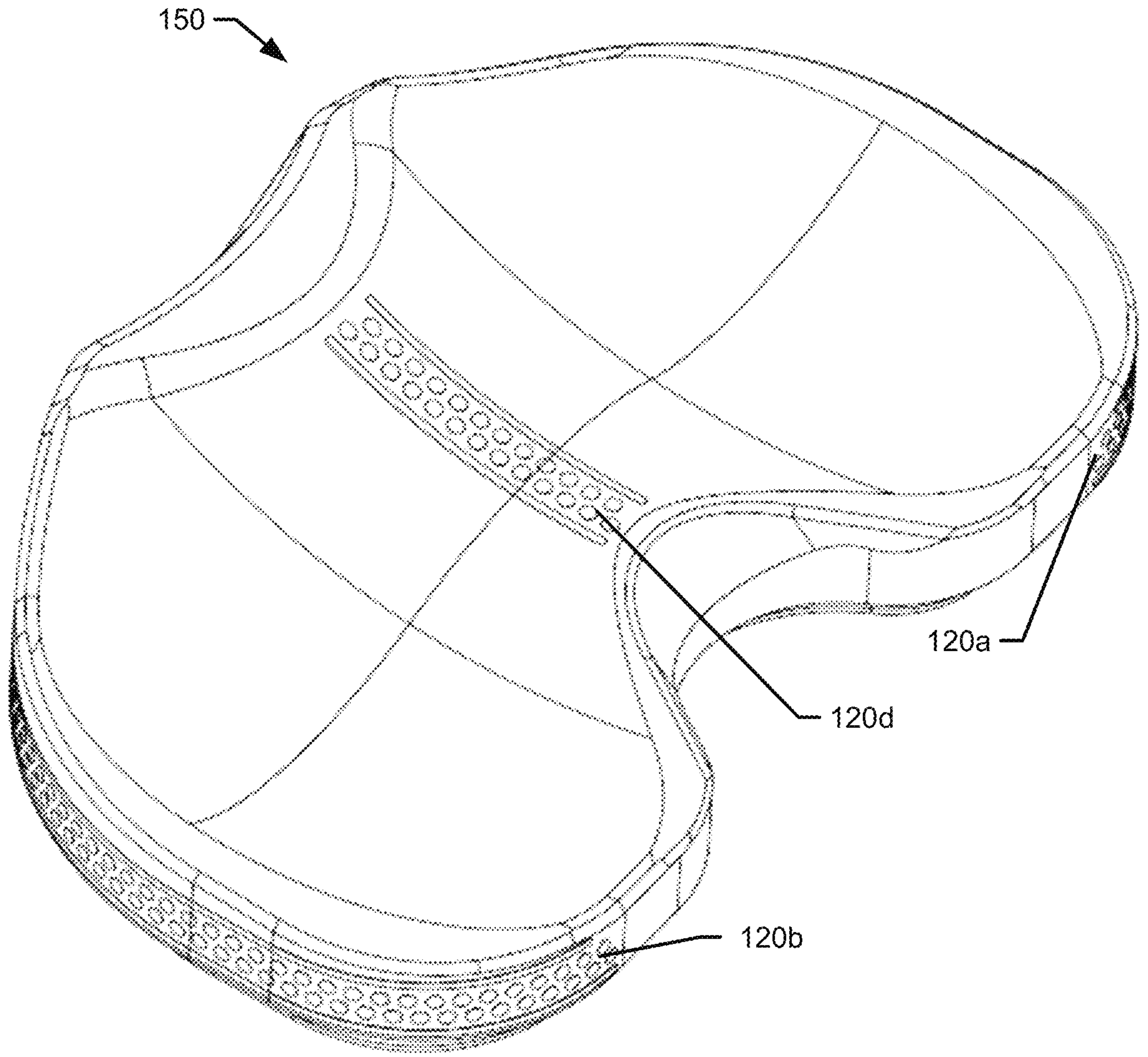
FIG. 6B illustrates yet another view of the tibial insert with two sets of RF-based biofilm sensors on either side of the tibial insert and a third sets of RF-based biofilm sensors centrally located on a top of the tibial insert, according to some embodiments of the present disclosure.

FIG. 6B illustrates yet another view of the tibial insert 150 with two sets of RF-based biofilm sensors 120*a*-*b* on either side of the tibial insert 150 and a third sets of RF-based biofilm sensors 120*d* centrally located on a top of the tibial insert 150, according to some embodiments of the present disclosure.

Figure 7:
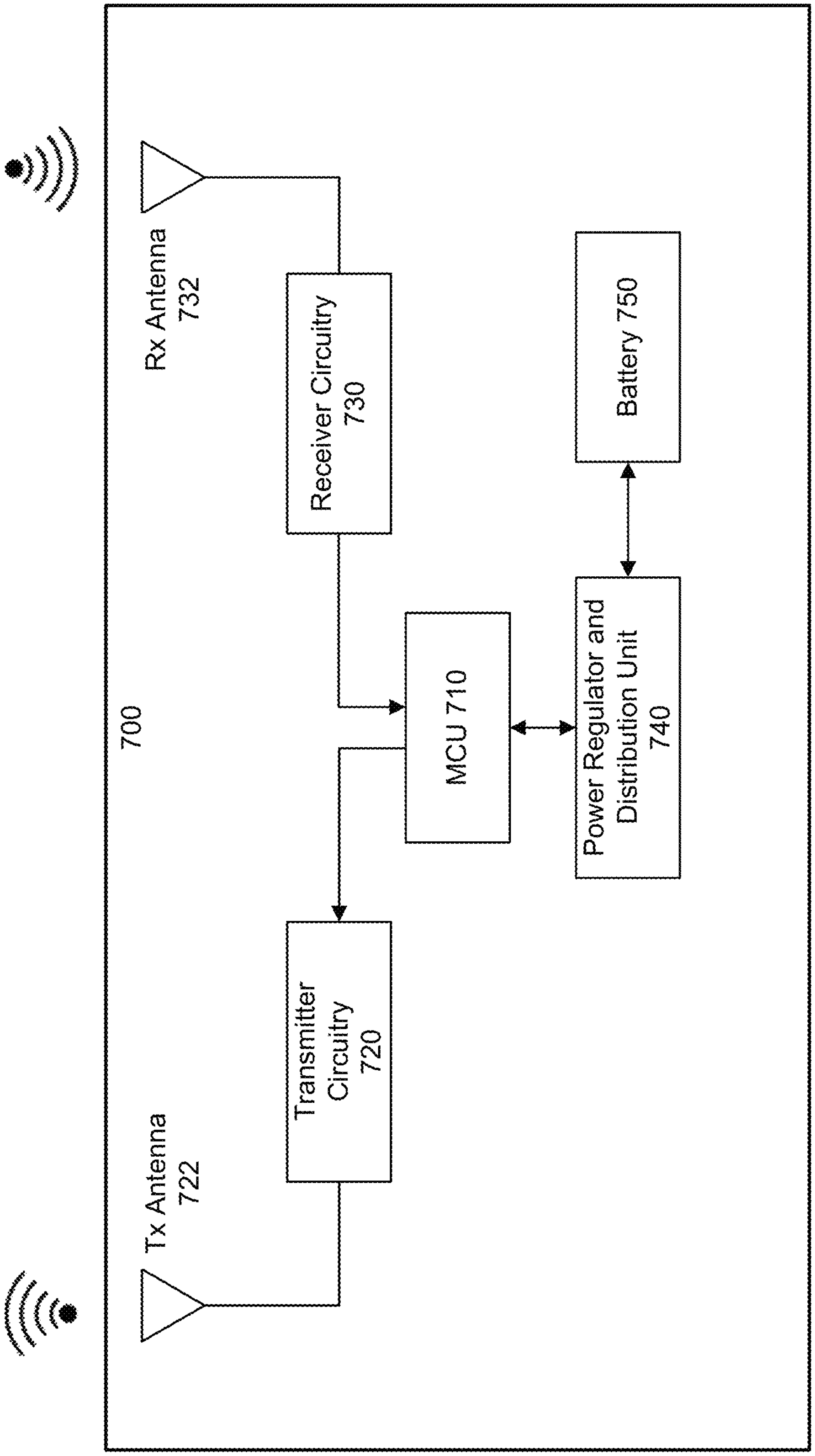
FIG. 7 illustrates a block diagram of an implantable RF-based biofilm sensor system, according to some embodiments of the present disclosure.

FIG. 7 illustrates a block diagram of an implantable RF-based biofilm sensor system 700, according to some embodiments of the present disclosure. The RF-based biofilm sensory system 700 may be housed in an implant component (e.g., tibial insert) of the medical implant and include a microcontroller unit (MCU) 710, a transmitter circuit 720, a transmit (Tx) antenna 722, a receiver circuit 730, a receiver (Rx) antenna 732, a power regulator and distribution unit 740, and a battery 750.

In some embodiments, the battery 750 may be the same or similar to energy storage device 230 of FIG. 2A. The MCU 710, power regulator and distribution unit 740, receiver circuit 730, and transmitter circuit 720 may be included in the circuitry 240 discussed above. The Tx antenna 722 may be the same or similar to the RF transmit antenna 320*a* discussed above. The Rx antenna 732 may be the same or similar to RF receive antenna 320*b* discussed above.

The battery 750 may power the other components in the RF-based biofilm sensory system 700. The power regulator and distribution unit 740 is connected to the battery 750 and the MCU 710 and may be configured, in connection with the MCU 710, to regulate and distribute power from the battery 750 to other components in the RF-based biofilm sensory system 700.

Both the Tx antenna 722 and receiver antenna 732 are connected to a processor unit (i.e., the MCU 710), which controls (i.e., generates) the transmitted RF signal and interprets the received RF signal. The MCU 710 executes a biofilm detection algorithm or instructions to process the RF signal to determine characteristics of attenuation that may indicate a presence, amount, and/or type of biofilm on the surface of the medical implant. However, a Rx antenna 732 and receiver circuit 730 may be optional, for example, in embodiments when the characteristic of attenuation of the RF signal is determined based on a reflected power of the RF signal provided by the MCU 710 toward the Tx antenna 722.

In some embodiments, the MCU may include one or more processors and may be operative to generate a RF signal to the Tx antenna 722, determine a characteristic of attenuation of the RF signal when the Tx antenna is transmitting the RF signal while implanted in the patient, and detect presence of biofilm based on the characteristic of attenuation of the RF signal.

The transmitter circuit 720 may convert power and/or signals received by the MCU 710 to signals that the Tx antenna 722 can transmit. The receiver circuit 730 may convert power and/or signals received from the Rx antenna 732 to signals the MCU 710 can receive.

In some embodiments, the Tx antenna 722 connected to a transmitter circuit 720 is capable of emitting a RF signal in the microwave RF spectrum. In a non-limiting example, the Tx antenna 722 may be able to emit a RF signal between 300 MHz and 3 GHz.

In some embodiments, the Rx antenna 732 connected to the receiver circuit 730 is operable in the same spectrum, for example, between 300 MHz and 3 GHz. The transmitted RF signal may consist of a sweep across discrete frequencies in the spectrum or a single signal at a specific frequency. In these embodiments, the MCU 710 may be further operative to generate a range of RF signals sweeping through a defined frequency range and/or a defined amplitude range, and detect the presence of biofilm based on identifying at least a threshold change in amplitude and/or frequency of the RF signals at one or more defined marker frequencies and/or defined marker amplitudes indicative of presence of a biofilm. The threshold change in amplitude and/or frequency may indicate a fingerprint for an amount and/or type of biofilm present due to certain amounts of biofilm and/or certain types (e.g., classes or species) of biofilm that attenuate the RF signal(s) at specific frequencies differently. Specific amounts (e.g., thickness and/or surface area covered, etc.) and/or types of biofilm may be known to attenuate the RF signal(s) in certain ways such as affecting the amplitude and/or frequency of the RF signal(s) (e.g., affecting impedance of the RF signal pathway) at certain frequencies. Different types of bacteria present in biofilm and/or different states of bacteria growth and biofilm formation (e.g., thickness and/or surface area covered, etc.) may be determined based on known relationships between RF transmit frequency and change in attenuation of the RF signal.

In one embodiment of the biofilm detection algorithm, the MCU 710 relates the change in frequency and change in amplitude of resonance received by the Rx antenna 732 to known states of bacteria growth and biofilm formation. The changes in these parameters are correlative to the changes in dielectric permittivity and dielectric loss of the adjacent fluid or substance associated with biofilm formation.

In some embodiments, S-parameters can be analyzed to evaluate this signal change associated with biofilm formation. According to antenna theory, S-parameters describe the input-output relationship between ports/terminals. In the RF-based biofilm sensory system 700, the transmitter circuit 720 and receiver circuit 730 would be considered ports that deliver power to the Tx antenna 722 and Rx antenna 732. Generally, the parameter Syx represents the power transferred from Port X to Port Y. In the RF-based biofilm sensory system 700, the S21 parameter represents the power transferred from Port 1 (transmitter) to Port 2 (receiver). In some embodiments, the characteristic of attenuation is the S21 parameter across a sweep of frequencies or at a specific frequency and compare the measurement to a calibration curve(s) (created as a result of performing the calibration operation(s)) associated with states of biofilm growth. Alternatively, the biofilm detection algorithm may measure the S21 parameter and compare the measurement to measurements taken over time and determine if there is a threshold difference between the S21 parameter and one or more of the measurements taken over time.

In some embodiments, the S11 parameter represents the reflected power that the transmitter circuit 720 is attempting to deliver to the Tx antenna 722. The S11 parameter is also referred to as the reflection coefficient, gamma, or return loss. Generally, antennas are designed to minimize the S11 parameter at the target frequency of use. The level of reflected power is related to impedance mismatch caused by biofilm being present, that results in bounce back of a portion of RF signal(s) conducted from the transmitter circuit 720 toward the Tx antenna 722 for transmission. S11 parameters are typically measured in dB as a function of frequency using a vector network analyzer system. In one embodiment, the RF-based biofilm sensory system 700 incorporates a vector network analyzer subsystem as part of the MCU 710 to measure the S11 parameter across a spectrum of frequencies or a specific frequency. In this configuration, the biofilm detection algorithm may measure the S11 parameter and compare the measurement to calibration curve(s) (created as a result of performing the calibration operation(s)) associated with states of biofilm growth. In these embodiments, the Rx antenna 732 and receiver circuit 730 may be optional. Alternatively, the biofilm detection algorithm may measure the S11 parameter and compare the measurement to measurements taken over time and determine if there is a threshold difference between the S11 parameter and one or more of the measurements taken over time.

In some embodiments, the MCU 710 is further operative to determine an amount of biofilm present based on the determined characteristic of attenuation of the RF signal. In some of these embodiments, the amount of biofilm present is determined proportional to an amount of attenuation of the RF signal between the RF transmit antenna (e.g., Tx antenna 722) and a RF receive antenna (e.g., Rx antenna 732) in the implant component and configured to receive the RF signal.

In some embodiments, the MCU 710 is further operative to determine a type of bacteria present in the biofilm based on the determined characteristic of attenuation of the RF signal. In some of these embodiments, the type of bacteria present in the biofilm is determined based on the characteristic of attenuation of the RF signal comprising a change in frequency of the RF signal between the RF transmit antenna and a RF receive antenna in the implant component and configured to receive the RF signal. For example, one type of bacteria or the fluid secrete therefrom can resonate at a defined frequency, and which then results in much greater attenuation of an RF signal having the defined frequency passing through the biofilm. The MCU 710 may be able to determine a type of bacteria based on observing change in the characteristic of attenuation (e.g., magnitude, phase shift, and/or frequency shift) of the RF signal when a defined RF signal frequency or range of RF signal frequencies is transmitted through that type of bacteria, where the change correlates to a known relationship attributable to that type of bacteria. Some examples of types of bacteria that may be measured or detected by the RF-based biofilm sensory system 700 include, but are not limited to, *Staphylococcus aureus, Staphylococcus epidermidis*, and *Streptococcus.*

In some embodiments, the MCU 710 is further operative to generate signaling indicating the characteristic of attenuation of the RF signal and/or indicating detection of presence of the biofilm to the RF transmit antenna (e.g., Tx antenna 722), for transmission to a clinician. For example, the MCU 710 can create a log of measured characteristics of attenuation (e.g., when a change in the measured characteristic of attenuation satisfies a defined rule) and transmit the log to a computing platform associated with the clinician, e.g., through a RF wireless link (Bluetooth) and one or more networks, e.g., public (Internet) and/or private networks. This provides the clinician with information important for diagnosis and treatment of PJI.

Further Definitions and Embodiments

It should be noted that the use of the term "characteristic" and "parameter" may be used interchangeably.

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, micro-code, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. A method of detecting an infection comprising:
- placing in a patient an implant including:
  - a radio frequency (RF) transmit antenna in the implant component and configured to transmit a RF signal; and
  - circuitry within the implant component and operative to generate the RF signal to the RF transmit antenna,
- determining, by the circuitry, a characteristic of attenuation of the RF signal when the RF transmit antenna is transmitting the RF signal while implanted in the patient, and
- detecting, by the circuitry, presence of biofilm on the medical implant based on the characteristic of attenuation of the RF signal.

2. The method of claim 1, wherein the implant includes a RF receive antenna spaced from the RF transmit antenna and configured to receive the RF signal, wherein the characteristic of attenuation of the RF signal is determined based on the RF signal characteristics received at the RF receive antenna.

3. The method of claim 2, wherein the implant includes electromagnetic field (EMF) shielding positioned between the RF transmit antenna and the RF receive antenna and configured to attenuate RF signaling along a direct pathway from the RF transmit antenna to the RF receive antenna through the EMF shielding.

4. The method of claim 2, wherein the RF transmit antenna and the RF receive antenna are spaced apart from each other along a surface of the medical implant.

5. The method of claim 2, wherein the RF transmit antenna and RF receive antenna are circular shaped and arranged concentrically with different diameters.

6. The method of claim 1, wherein determining a characteristic of attenuation of the RF signal includes determining based on a reflected power of the RF signal provided by the circuitry toward the RF transmit antenna.

7. The method of claim 1, wherein determining a characteristic of attenuation of the RF signal includes determining based on at least one of power transferred by the RF signal from the RF transmit antenna to a RF receive antenna in the implant and configured to receive the RF signal, a change in frequency between the RF signal transmitted by the RF transmit antenna and the RF signal received by the RF receive antenna, and a change in amplitude between the RF signal transmitted by the RF transmit antenna and the RF signal received by the RF receive antenna, a change in phase between the RF signal transmitted by the RF transmit antenna and the RF signal received by the RF receive antenna.

8. The method of claim 1, wherein detecting the presence of biofilm includes comparing the determined characteristic of attenuation of the RF signal to a threshold characteristic of attenuation defined based on a calibration measurement operation.

9. The method of claim 1, wherein detecting the presence of biofilm includes comparing the characteristic of attenuation of the RF signal to at least one prior characteristic of attenuation, and determining that biofilm is present based on the characteristic of attenuation of the RF signal being a threshold difference than the prior characteristic of attenuation.

10. The method of claim 1, wherein the circuitry is further operative to:
- generate a range of RF signals sweeping through a defined frequency range and/or a defined amplitude range; and
- detect the presence of biofilm based on identifying at least a threshold change in amplitude and/or frequency of the RF signals at one or more defined marker frequencies and/or defined marker amplitudes indicative of presence of a biofilm.

11. The method of claim 1, wherein the circuitry is further operative to determine an amount of biofilm present based on the determined characteristic of attenuation of the RF signal.

12. The method of claim 11, wherein the amount of biofilm present is determined proportional to an amount of attenuation of the RF signal between the RF transmit antenna and a RF receive antenna in the implant and configured to receive the RF signal.

13. The method of claim 1, wherein the circuitry is further operative to determine a type of bacteria present in the biofilm based on the determined characteristic of attenuation of the RF signal.

14. The method of claim 13, wherein the type of bacteria present in the biofilm is determined based on the characteristic of attenuation of the RF signal comprising a change in frequency of the RF signal between the RF transmit antenna and a RF receive antenna in the implant component and configured to receive the RF signal.

15. The method of claim 1, wherein the RF transmit antenna is recessed in the implant, and the implant further comprises a RF window extending across the RF transmit antenna and separating the antenna from fluid and/or tissue while the implant is implanted in the patient.

16. The method of claim 15, wherein the RF window has a rougher surface, exposed to the patient, than an adjacent surface of the implant component exposed to the patient to promote earlier formation of biofilm on the rougher surface of the RF window.

17. The method of claim 1, wherein circuitry is further operative to generate signaling indicating the characteristic of attenuation of the RF signal and/or indicating detection of presence of the biofilm to the RF transmit antenna, for transmission to a clinician.

* * * * *